United States Patent [19]
Lewis et al.

[11] Patent Number: 5,420,136
[45] Date of Patent: May 30, 1995

[54] ERADICATION OF PATHOGENIC BIOLOGICAL CONTAMINANTS USING NON-AZO NAPHTHALIMIDE DYES

[75] Inventors: David E. Lewis, Brookings; Ronald E. Utecht, Volga, both of S. Dak.; Millard M. Judy; J. Lester Matthews, both of Dallas, Tex.

[73] Assignee: MicroBioMed Corporation, Dallas, Tex.

[21] Appl. No.: 103,924

[22] Filed: Aug. 9, 1993

Related U.S. Application Data

[62] Division of Ser. No. 854,416, Mar. 19, 1992, Pat. No. 5,235,045.

[51] Int. Cl.$^6$ ............... A61K 31/435; A61K 31/535; A61K 31/54; A61K 39/00
[52] U.S. Cl. .................... 514/296; 424/1.17; 424/1.33; 424/1.49; 424/1.65; 424/1.81; 514/284; 514/885; 546/76; 546/77; 546/97; 546/22; 546/23; 546/88; 546/98; 546/100; 546/13; 546/14; 540/467
[58] Field of Search ........... 514/296, 284, 885; 546/22, 23, 88, 97, 98, 100, 77, 76; 424/1.17, 1.33, 1.49, 1.65, 1.81

[56] References Cited

U.S. PATENT DOCUMENTS

| | | | |
|---|---|---|---|
| 3,959,286 | 5/1976 | Wade et al. | 401/166 |
| 4,006,238 | 2/1977 | Wade | 514/296 |
| 4,062,953 | 12/1977 | Wade et al. | 514/296 X |
| 4,594,346 | 6/1986 | Zee-Cheng et al. | 514/237 |
| 4,874,863 | 10/1989 | Brana et al. | 544/99 |
| 4,878,891 | 11/1989 | Judy et al. | 604/5 |
| 5,086,059 | 2/1992 | Ardecky et al. | 514/284 |
| 5,091,385 | 2/1992 | Gulliya | 514/228.4 |
| 5,177,083 | 1/1993 | Rideout et al. | 514/296 |
| 5,183,821 | 2/1993 | Brana et al. | 514/296 |
| 5,206,249 | 4/1993 | Sun | 514/296 |
| 5,206,250 | 4/1993 | Sun | 514/296 |

FOREIGN PATENT DOCUMENTS

3635711A1  4/1988  Germany ............ 514/228.4

*Primary Examiner*—Floyd D. Higel
*Attorney, Agent, or Firm*—Konneker, Bush Hitt & Chwang

[57] ABSTRACT

A class of predominantly hydrophobic non-azo N-substituted 1,8-naphthalimide compounds, each bearing, at its 3-position, a nucleofuge and, at its 4-position, a heteroatomic electron-releasing group. The heteroatomic electron-releasing group is being characterized as having a heteroatom directly linked to the 4-position of the ring, and having at least one hydrogen directly attached to the heteroatom. Upon activation by an activating agent in an environment independent of the presence or absence of oxygen, these compounds generate activated species. The activated species initiate chemical changes in lipid bilayer membranes of viruses and other target cells. These changes can eradicate viruses and other target cells. The activated species can also cause structural changes in lipid and any associated proteins and polypeptides at a level beneath the surface of the membrane, leading to polymerization and cross-linking.

24 Claims, 15 Drawing Sheets

I

II

III

IV

XXIX

XXX

XXXI

XXXII

XXXVII

XXXVIII

XXXIX

XL

XLIII

XLIV

XLV

XLVII

XLVIII

XLIX

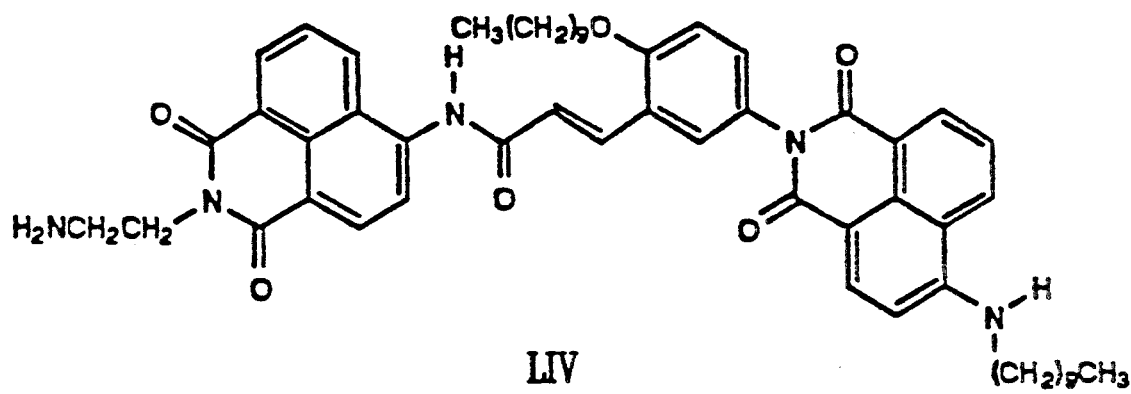
LIV
*Figure 1aaa*
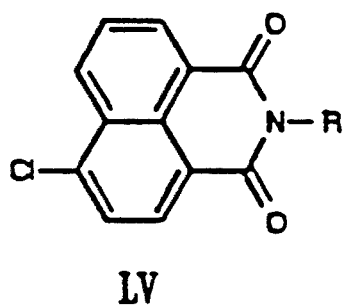
LV
*Figure 1bbb*
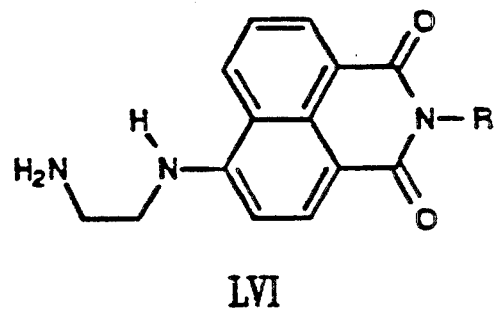
LVI
*Figure 1ccc*

ERADICATION OF PATHOGENIC BIOLOGICAL CONTAMINANTS USING NON-AZO NAPHTHALIMIDE DYES

This is a divisional of application Ser. No. 07/854,416 filed on Mar. 19, 1992, now U.S. Pat. No. 5,235,045.

FIELD OF THE INVENTION

The present invention relates to predominantly hydrophobic non-azo 1,8-naphthalimide dyes, their compositions, their preparations, and their uses. More specifically, the present invention relates to predominantly hydrophobic monomeric and dimeric non-azo N-substituted-1,8-naphthalimide dyes, their compositions, their preparations, and their uses.

Classical photodynamic therapy, which superficially resembles the new invention described herein is a technique by which membrane alterations can be made in a living cell and virus envelope by irradiation of a dye incorporated into the membrane. See, U.S. Pat. Nos. 4,613,322; 4,684,521; 4,649,151; and 4,878,891. This classical technique has been proven to rely on the triplet sensitization of oxygen to form singlet oxygen within the membrane. The hydroperoxides produced in the initial reaction between singlet oxygen and the unsaturated lipids of the membrane decompose to produce the observed membrane alterations, leading to cell death or viral inactivation. Thus, the efficiency of the photodynamic effect is directly related to the efficiency of the classical dyes as a triplet sensitizer. Nearly all dyes currently used for the classical photodynamic therapy give good triplet yields upon irradiation. While selective alteration of either plasma or mitochondrial membranes can be achieved by using a dye with appropriate localization characteristics, the actual chemistry which produces the modification cannot be well controlled, and selective damage to the membrane cannot be affected.

There is currently no method available for selectively altering a membrane based upon selecting for one membrane over another on the basis of any simple membrane property, such as lipid composition, membrane fluidity, surface proteins, integral proteins, or other similar features. Moreover, all effective photochemical inactivators published to date rely on the production of singlet oxygen and the uncontrolled free-radical chemistry of the hydroperoxides which it produces to achieve the cell kill or viral inactivation.

SUMMARY

According to the present invention, new non-azo 1,8-naphthalimide dyes or compounds are provided. These dyes can be "monomeric" or "dimeric." Further, their different uses are given. These new non-azo 1,8-naphthalimide dyes are predominantly hydrophobic and, and after being activated by a sufficient amount of activating agent in an environment independent of the presence or absence or oxygen, give activated derivatives or species. More specifically, the present invention relates to a "monomeric" non-azo N-substituted-1,8-naphthalimide compound bearing, at a 3-position, a nucleofuge and, at a 4-position, a heteroatomic electron-releasing group, which is being characterized as having a heteroatom directly linked to the 4-position, and having at least one hydrogen directly attached to the heteroatom. The present invention also relates to a predominantly hydrophobic "dimeric" non-azo bis-naphthalimide compound, having at least two 1,8-naphthalimide moieties each bearing, at a 3-position, a nucleofuge and, at a 4-position, a heteroatomic electron-releasing group which is being characterized as having a heteroatom directly linked to the 4-position and having at least one hydrogen directly attached to the heteroatom. The bis-naphthalimide compound is further characterized as giving an activated derivative after being activated by a sufficient amount of activating agent in an environment independent of the presence or absence of oxygen. A non-azo compound or dye is one that does not possess a functional grouping having two nitrogen atoms connected by a double bond. A nucleofuge is any group which can be displaced from a molecule by a nucleophile. Examples of nucleofuge includes halogens, sulfonate esters, quartenary ammonium salts.

These new non-azo 1,8-naphthalimide dyes can be activated in the simultaneous presence of an activating agent and the target tissue or organism. Alternatively, these dyes can be pre-activated, in that they can first be activated with an activating agent, and then introduced to the target tissue or organism to accomplish their function in the absence of the activating agent.

Exemplary uses of these dyes include:

Fluorescent probes. The unhalogenated naphthalimide dyes are highly fluorescent lipophilic probes of low toxicity for the study of lipids in living systems, including plasma membranes, organellar membranes, lipoprotein and atherosclerotic plaques without requiring either prior covalent modification or fixation of the system being observed.

Protein immobilization. The immobilization of membrane-bound proteins, including surface antigens, glycoproteins, ionic channels, polypeptides, and enzymes in bilayers or micelles or both natural and synthetic lipids. The immobilization of surface antigens can occur in bilayers derived from a biological source. These immobilized species have the following uses: elicitation of an immune response to the bound species; and development of new whole-virus, subunit, bacterial and cell vaccines.

Stabilization of lipid bilayers or micelles. These stabilized bilayers or micelles have the following potential uses: (i) applications to dialysis; (ii) drug delivery, such as in stabilized liposomes; (iii) artificial semi-permeable membranes; (iv) biocompatible coatings, both biodegradable and non-biodegradable; (v) catalysis by bound species such as enzymes; (vi) construction of stabilized membrane-bound receptors for sensing applications; and (vii) energy production by charge separation or generation of concentration gradients mediated by bound proteins, porphyrins, or other photoactivatable species.

Organism death and viral inactivation induced by an activating agent. The incorporation of these dyes into lipid bilayer membranes allows the following uses: (i) sterilization of blood and blood products by selective incorporation into pathogenic organisms and light-induced pathogen inactivation; (ii) sterilization of materials where the presence of membrane-containing pathogens can be detrimental; and (iii) a new photochemical treatment, different from the classical photodynamic therapy, of certain cancers and tumors.

Encapsulation. Stabilized liposomes generated using these dyes to cross-link protein-containing liposomes can be used as encapsulating agents whose resistance to heat, physical stress, pH, evaporation, lyophilization, detergents, freezing, high ionic strength solutions, agitation, organic solvents, lipases and proteases is much superior to available liposome technology. Potential uses of such encapsulated materials include: (i) lyophilizable synthetic erythrocyte replacement (encapsulated hemoglobin); (ii) stabilized enzymes for organic synthesis, including asymmetric synthesis of drugs in both aqueous and organic solvent environments; (iii) time-release drug delivery where the rate of delivery is determined by the concentration of the drug, the time since administration, and the extent of crosslinking of the membrane; (iv) stabilized enzymes for therapeutic treatment of enzyme deficiency diseases; (v) stabilized encapsulated ion-selective complexing agents such as EDTA (ethylenediamine tetracecetic acid) for the treatment of diseases caused by an excess of a particular cation or anion.

DETAILED DESCRIPTION OF THE INVENTION

Figure 1A:
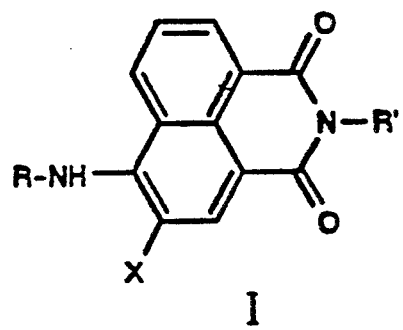
FIGS. 1 $a$ to 1 $z$, 1 $aa$ to $zz$, and 1 $aaa$ to 1 $ccc$ show the structural formula of Compounds I through LVI, respectively.
Figure 1B:
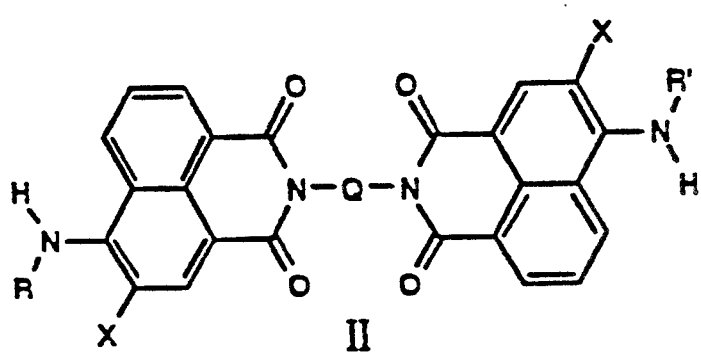
Figure 1C:
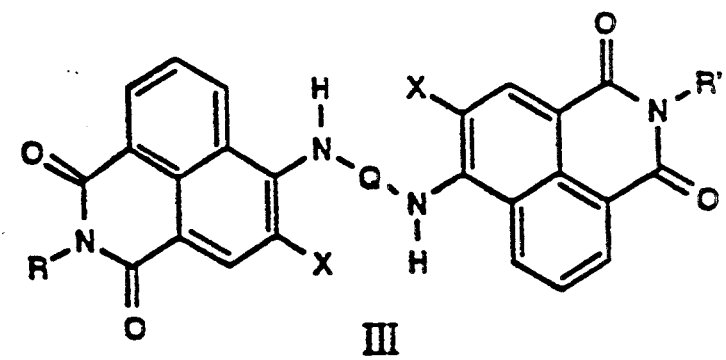
Figure 1D:
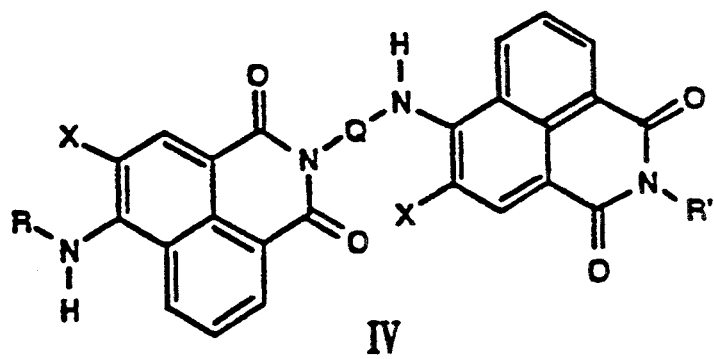
Figure 1E:
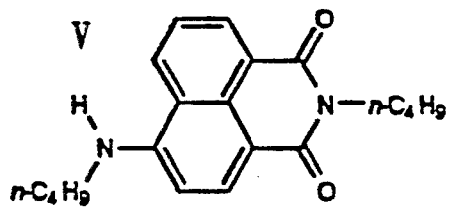
Figure 1F:
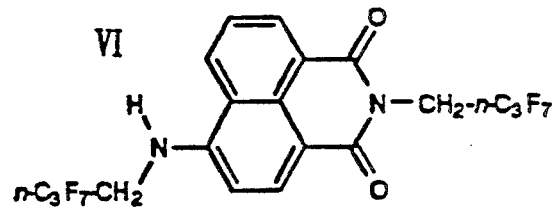
Figure 1G:
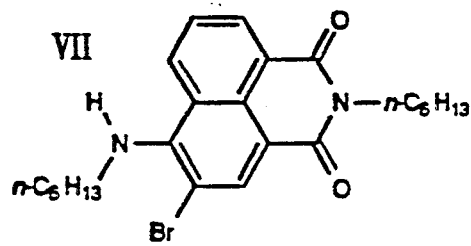
Figure 1H:
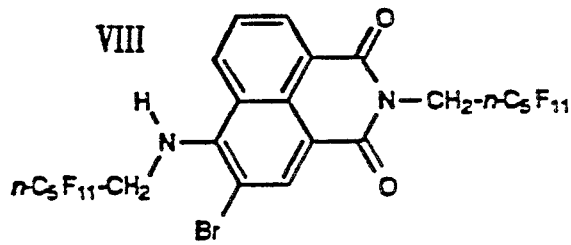
Figure 1I:
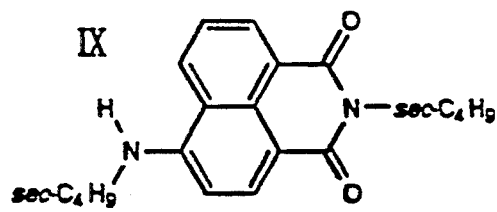
Figure 1J:
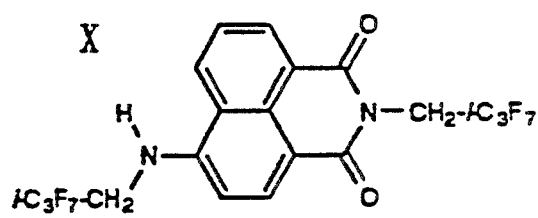
Figure 1K:
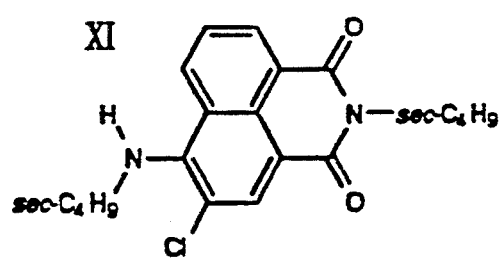
Figure 1L:
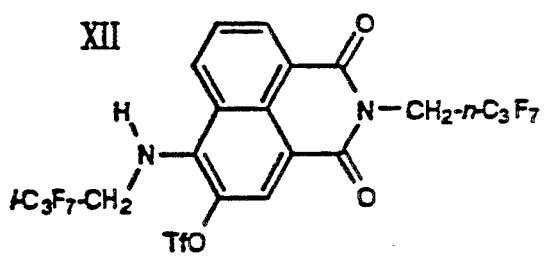
Figure 1M:
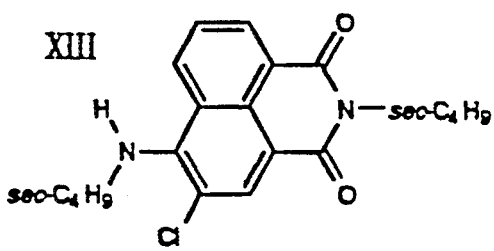
Figure 1N:
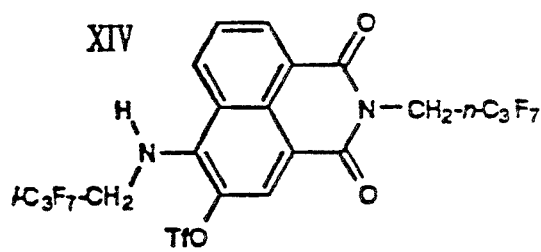
Figure 1O:
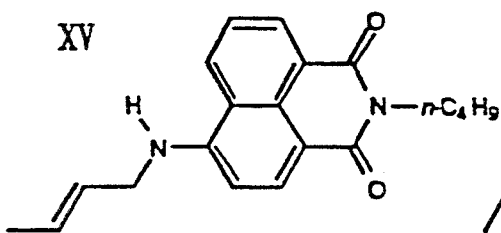
Figure 1P:
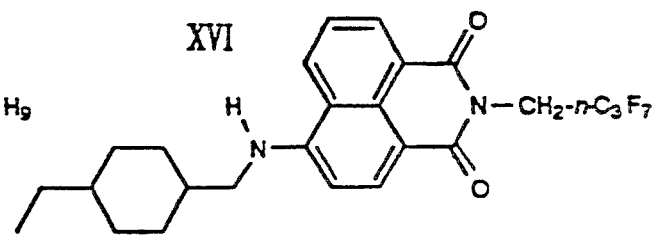
Figure 1Q:
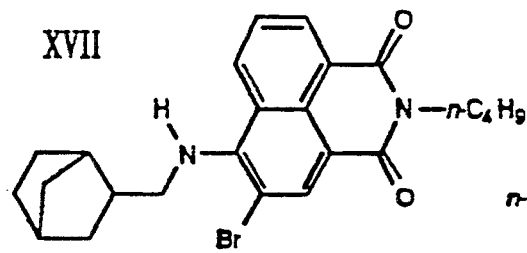
Figure 1R:
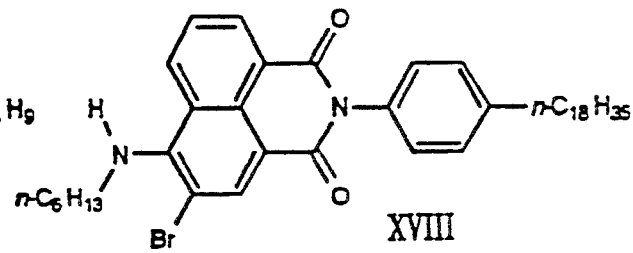
Figure 1S:
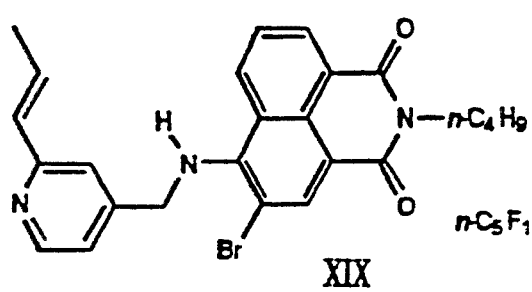
Figure 1T:
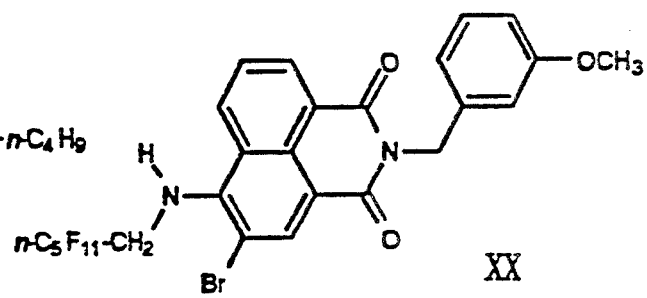
Figure 1U:
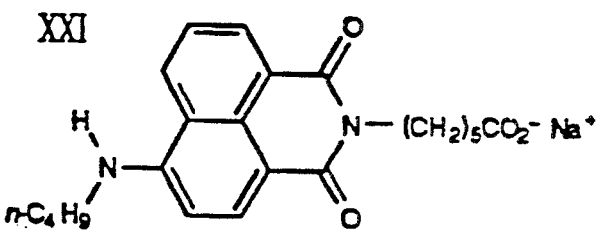
Figure 1V:
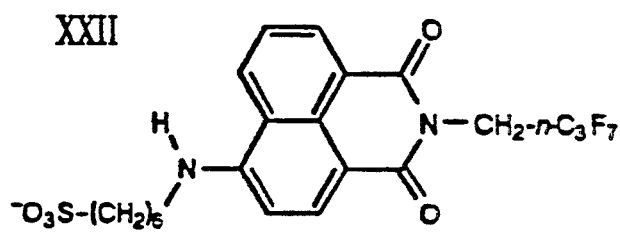
Figure 1W:
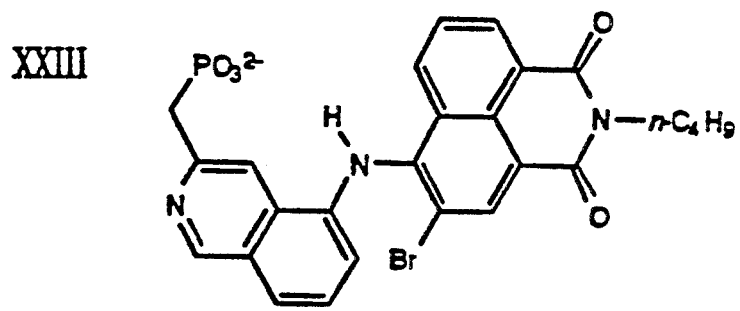
Figure 1X:
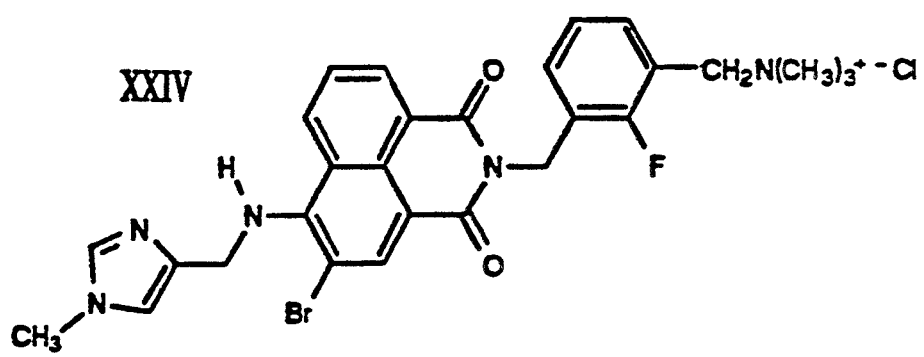
Figure 1Y:
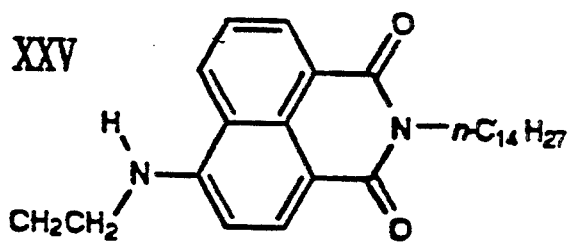
Figure 1Z:
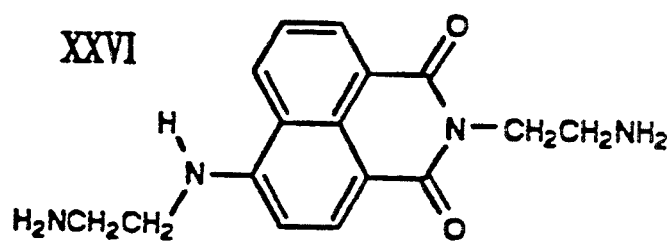
Figure 1A:
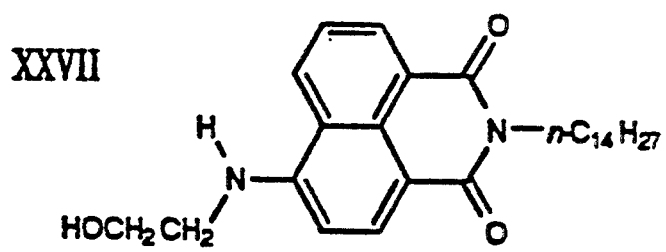
Figure 1B:
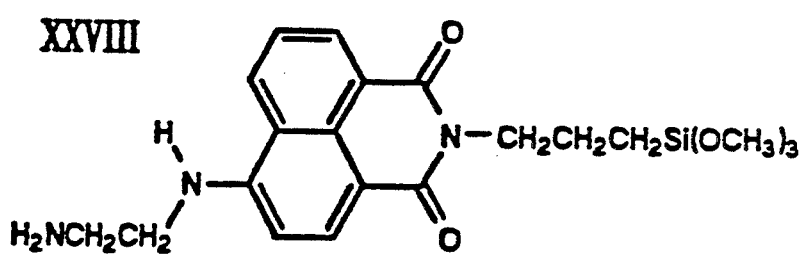
Figure 1C:
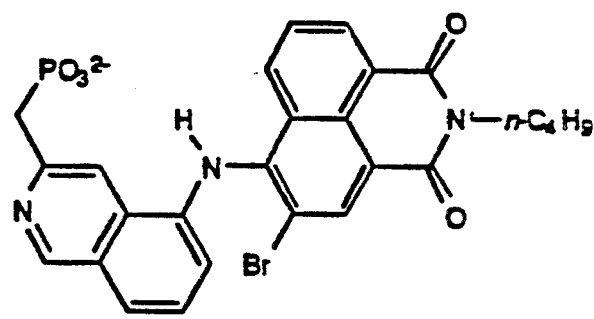
Figure 1D:
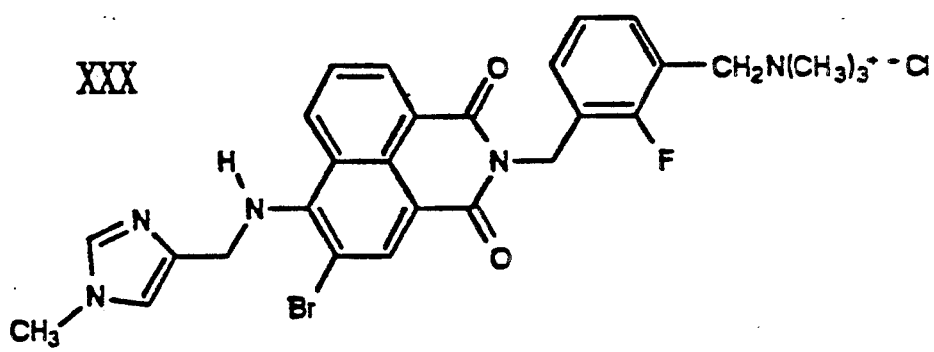
Figure 1E:
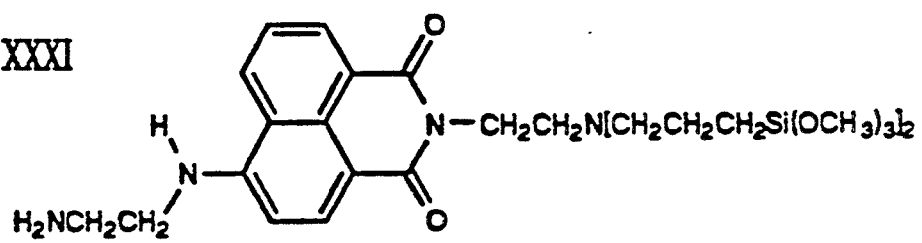
Figure 1F:
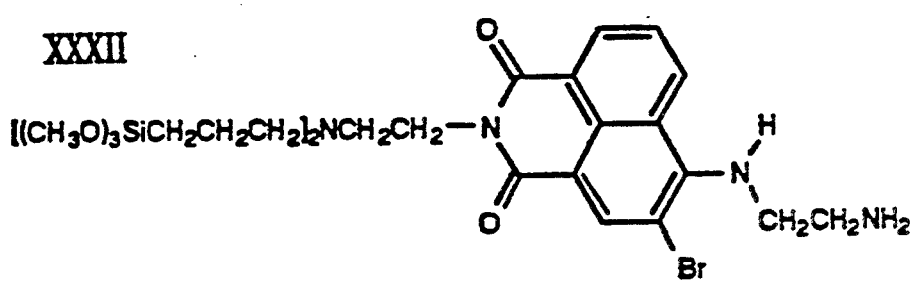
Figure 1G:
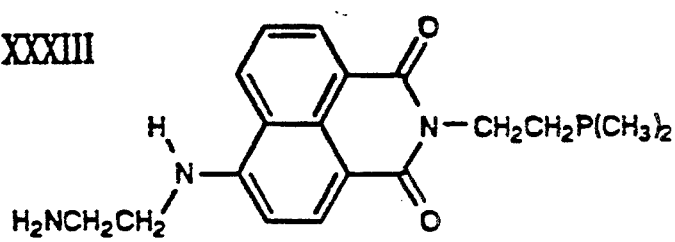
Figure 1H:
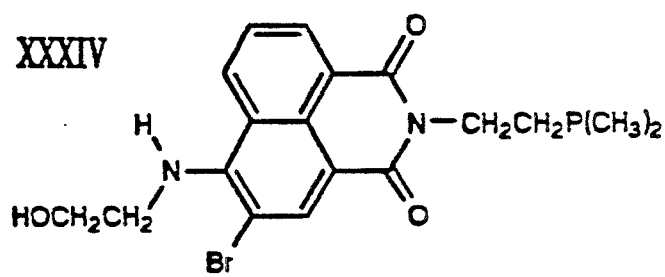
Figure 1I:
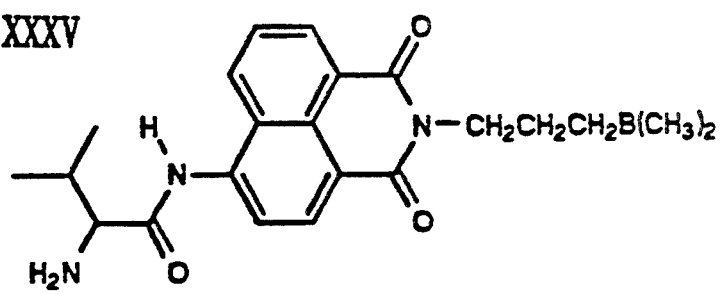
Figure 1J:
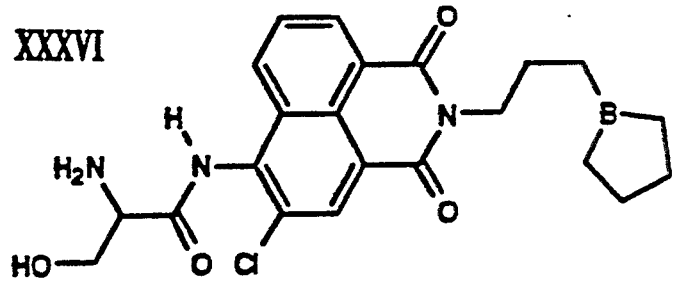
Figure 1K:
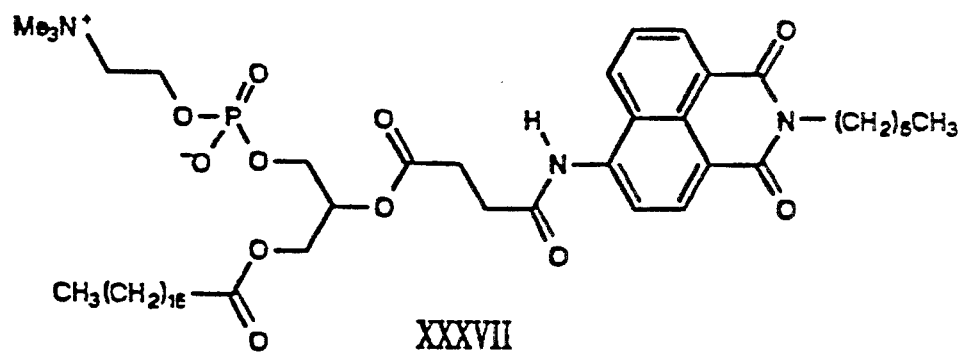
Figure 1L:
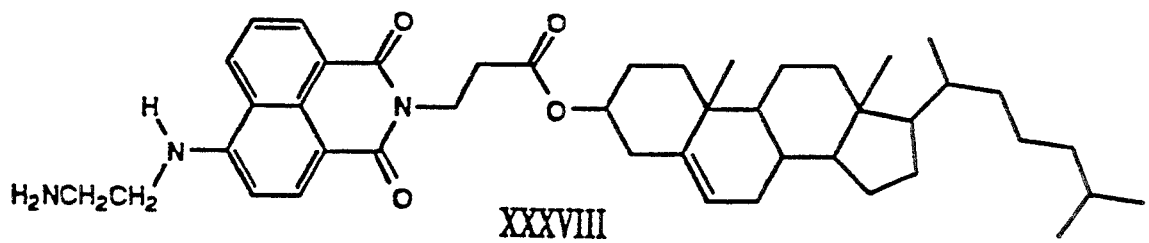
Figure 1M:
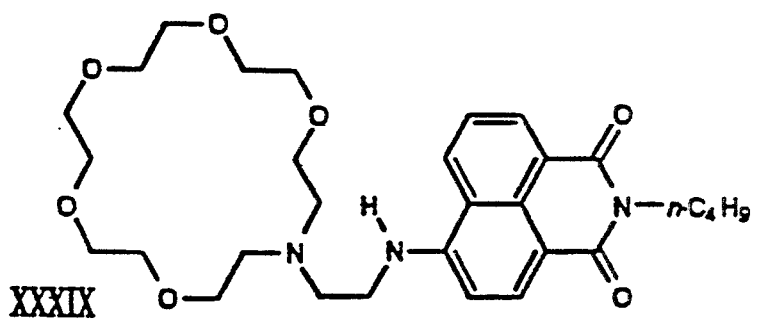
Figure 1N:
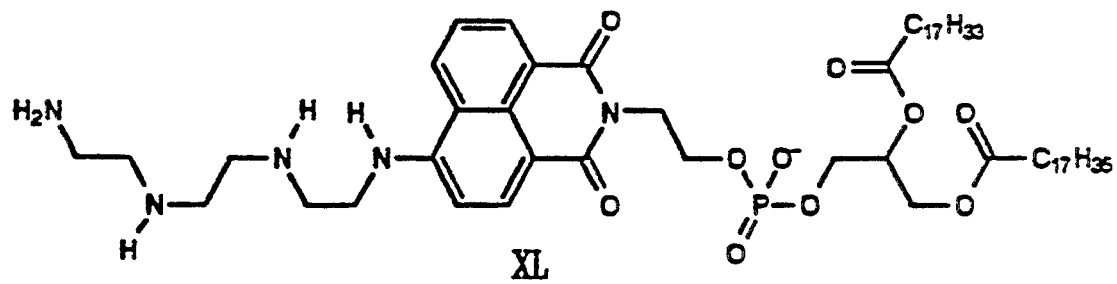
Figure 1O:
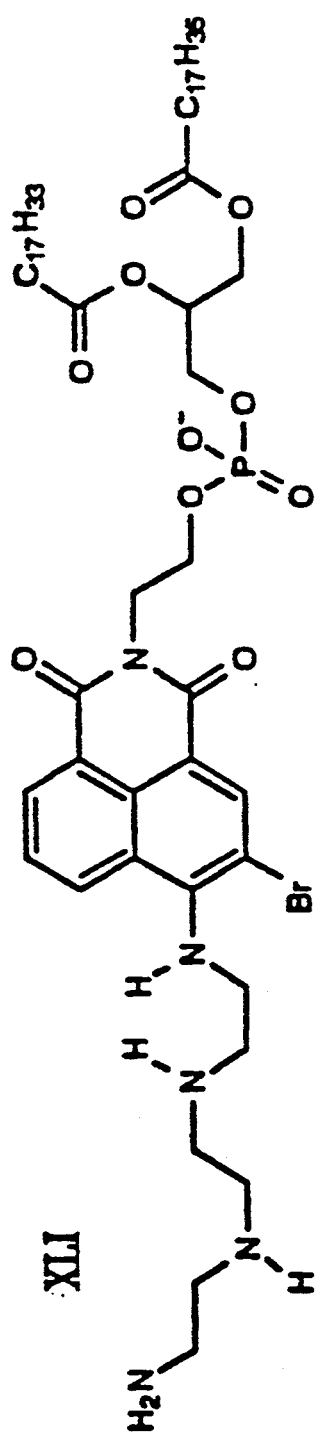
Figure 1P:
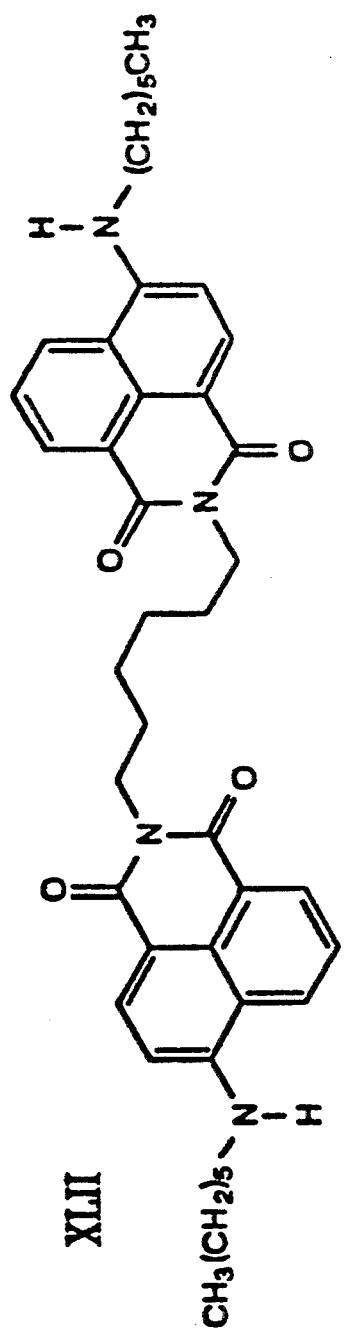
Figure 1Q:
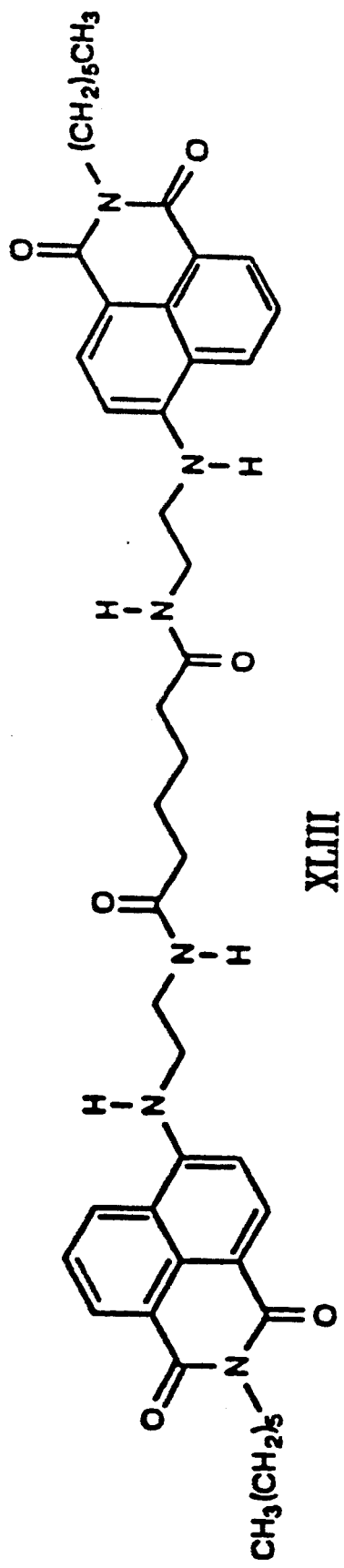
Figure 1R:
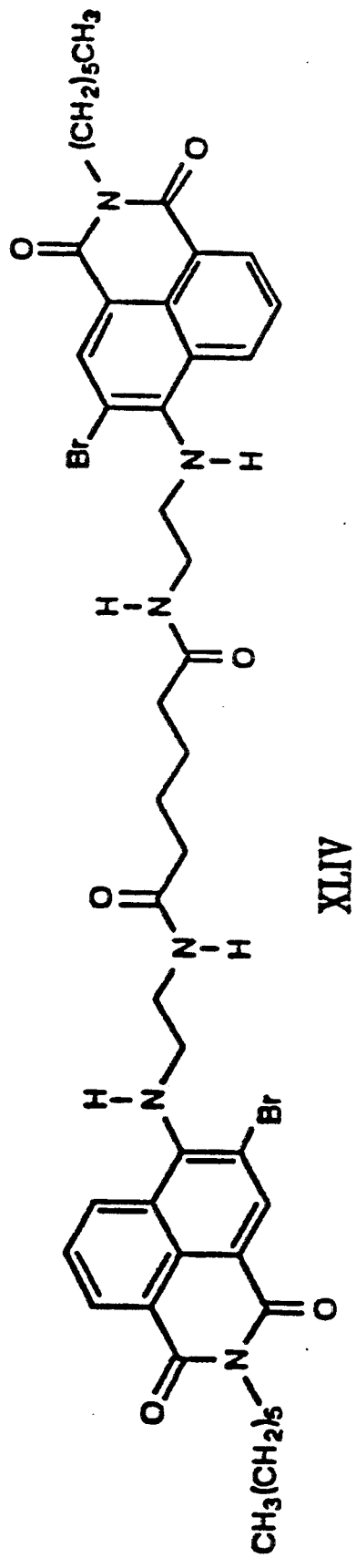
Figure 1S:
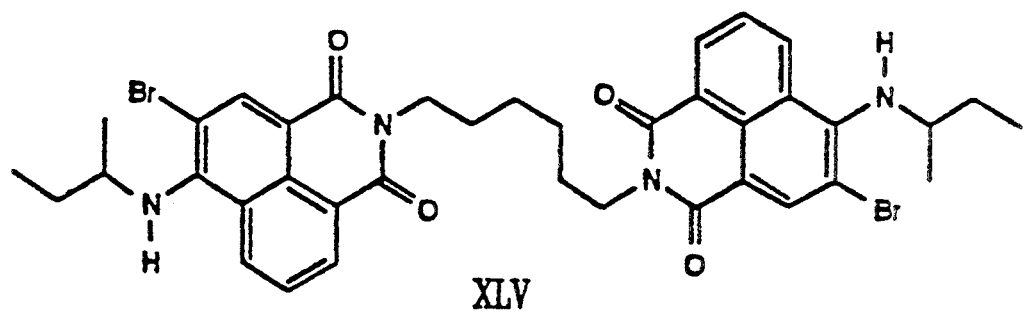
Figure 1T:
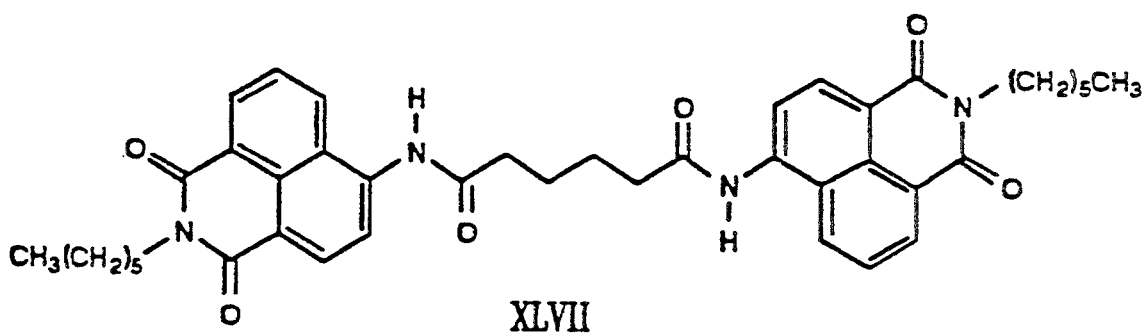
Figure 1U:
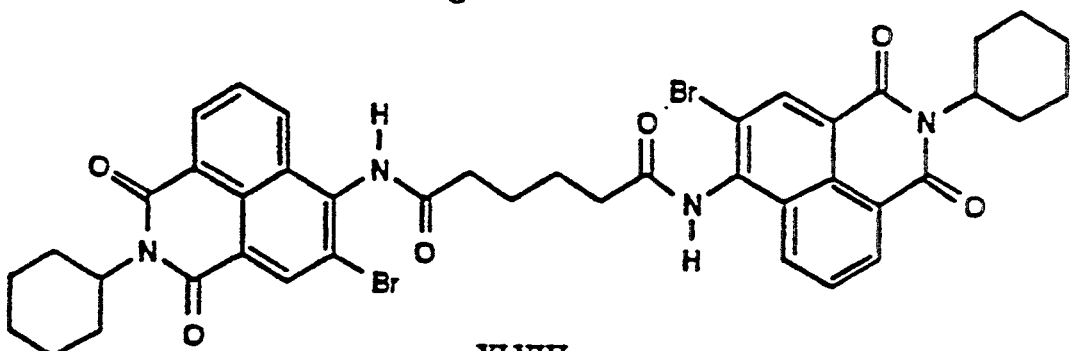
Figure 1V:
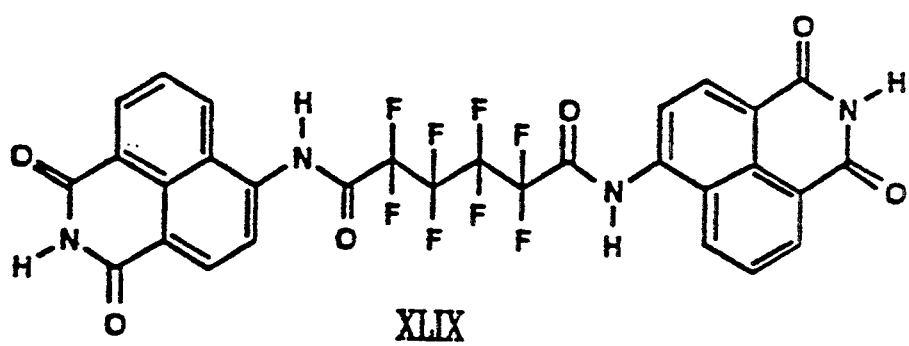
Figure 1W:
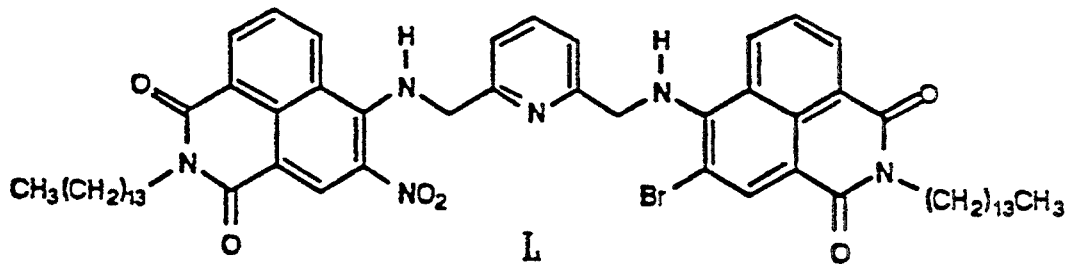
Figure 1X:
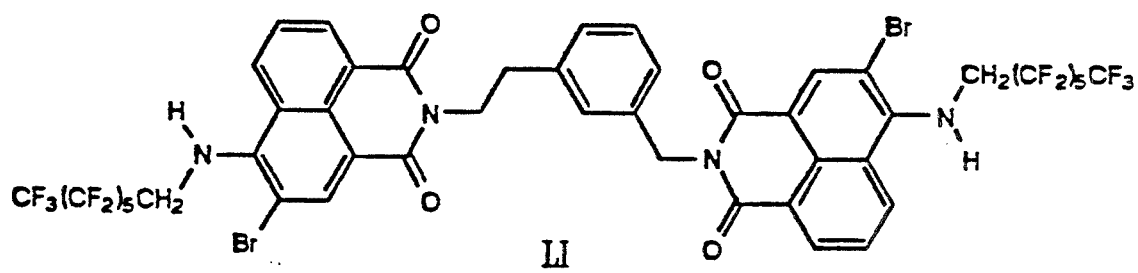
Figure 1Y:
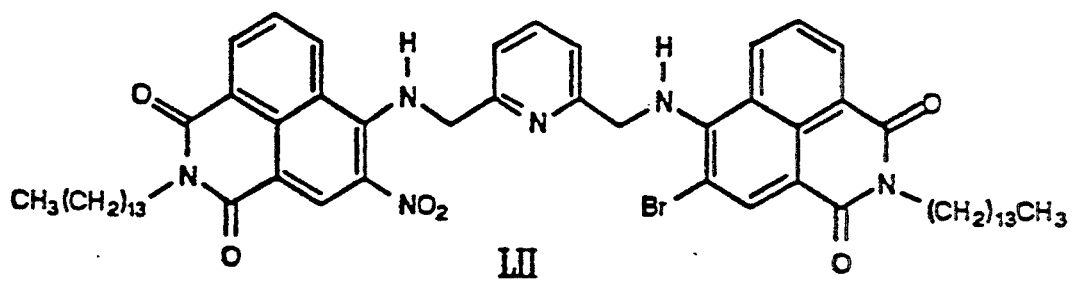
Figure 1Z:
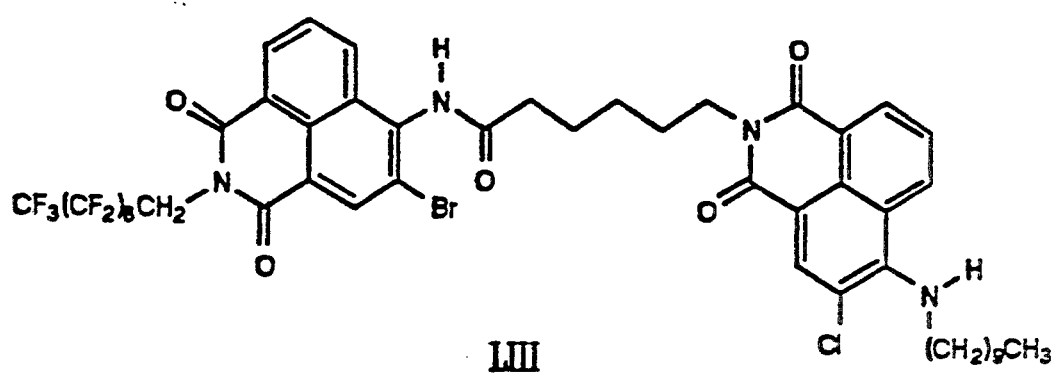

The generic formula for "monomeric" non-azo 1,8-naphthalimide dye is represented by Compound I, having mixtures of stereoisomers, wherein:

R and R':

saturated straight-chain or branched-chain alkyl, $C_nH_{2n+1}$ (n=1–30);

partially or totally fluorinated saturated straight-chain or branched-chain alkyl, $C_nH_qF_{2n-q+1}$ (n=1–30, $0 \leq q \leq 2n$);

unsaturated straight-chain or branched-chain alkyl, $C_nH_{2m+1}$ (n=1–30, $1 \leq m < n$);

partially or totally fluorinated unsaturated straight-chain or branched-chain alkyl, $C_nH_qF_{2m-q+1}$ (n=1–30, $1 \leq m < n$, $0 \leq q \leq 2m$);

alicyclic (monocyclic or polycyclic, fused-ring, bridged-ring or spirocyclic) alkyl, $C_nH_{2m+1}$ (n=1–30, $1 \leq m \leq n$) with saturated or unsaturated side-chains (branched or unbranched);

partially or totally fluorinated alicyclic (monocyclic or polycyclic, fused-ring, bridged-ring or spirocyclic) alkyl, $C_nH_qF_{2m-q+1}$ (n=1–30, $1 \leq m < n$, $0 \leq q \leq 2m$) with saturated or unsaturated side-chains (branched or unbranched);

aryl substituted branched, unbranched or alicyclic, saturated or unsaturated alkyl, $ArC_nH_{2m+1}$ (n=1–30, $1 \leq m \leq n$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

partially or totally fluorinated aryl substituted branched, unbranched or alicyclic, saturated or unsaturated alkyl, $ArC_nH_qF_{2m-q+1}$ (n=1–30, $1 \leq m \leq n$, $0 \leq q \leq 2m$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

substituted saturated straight-chain or branched-chain alkyl, $C_nH_{2n-p+1}Y_p$ (n=1–30, $1 \leq p \leq 10$) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated straight-chain or branched-chain alkyl, $C_nH_qF_{2n-p-q+1}Y_p$ (n-1–30, $1 \leq p \leq 10$ $0 \leq q \leq 2n$);

substituted unsaturated straight-chain or branched-chain alkyl, $C_nH_{2m-p+1}Y_p$ (n=1–30, $1 \leq m < n$, $1 \leq p \leq 10$) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated straight-chain or branched-chain alkyl, $C_nH_qF_{2m-p-q+1}Y_p$ (n=1–30, $1 \leq m < n$, $1 \leq p \leq 10$, $0 \leq q \leq 2m$);

substituted alicyclic (monocyclic or polycyclic, fused-ring, bridged-ring or spirocyclic) alkyl, $C_nH_{2m+1}$ (n=1–30, $1 \leq m \leq n$) with saturated or unsaturated side-chains (branched or unbranched) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated alicyclic (monocyclic or polycyclic, fused-ring, bridged-ring or spirocyclic) alkyl, $C_nH_qF_{2m-p-q+1}Y_p$ (n=1–30, $1 \leq m < n$, $1 \leq p \leq 10$ $0 \leq q \leq 2m$) with saturated or unsaturated side-chains (branched or unbranched) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted aryl substituted branched, unbranched or alicyclic, saturated or unsaturated alkyl, $ArC_nH_{2m-p+1}Y_p$ (n=1–30, $1 \leq m \leq n$, $1 \leq p \leq 10$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus, and where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated aryl substituted branched, unbranched or alicyclic, saturated or unsaturated alkyl, $ArCH_qF_{2m-p-q+1}Y_p$ ($n=1-30$, $1 \leq m \leq n$, $1 \leq p \leq 10$, $0 \leq q \leq 2m$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus, and where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

a straight-chain or branched-chain group capable of complexing a metal ion, $C_nH_{2m+1}Y_q$ ($n=1-30$, $1 \leq q \leq n$, $1 \leq q \leq n/2$), where Y is O, S, Se, NH, N-R, N-Ar, PH, P-R and/or P-Ar and their acyl (including aminoacyl and peptide) derivatives, and where R is saturated alkyl ($C_nH_{2n+1}$, $n=1-30$), fluorinated saturated alkyl ($C_nH_qF_{2n-q+1}$, $n=1-30$, $0 \leq q \leq 2n$), unsaturated alkyl ($C_nH_{2m+1}$, $n=1-30$, $1 \leq m < n$), fluorinated unsaturated alkyl ($C_nH_qF_{2m-q+1}$, $n=1-30$, $1 \leq m < n$, $0 \leq q \leq 2m$), alicyclic ($C_nH_{2m+1}$, $n=1-30$, $1 \leq m \leq n$), fluorinated alicyclic ($C_nH_qF_{2m-q+1}$, $n=1-30$, $1 \leq m < n$, $0 \leq q \leq 2m$), and where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

a substituted alicyclic group capable of complexing a metal ion, $C_nH_{2m+1}Y_q$ ($n=1-30$, $1 \leq q \leq n$, $1 \leq q \leq n/2$), where Y is O, S, Se, NH, N-R, N-Ar, PH, P-R and/or P-Ar and their acyl (including aminoacyl and peptide) derivatives, and where R is saturated alkyl ($C_nH_{2n+1}$, $n=1-30$), fluorinated saturated alkyl ($C_nH_qF_{2n-q+1}$, $n=1-30$, $0 \leq q \leq 2n$), unsaturated alkyl ($C_nH_{2m+1}$, $n=1-30$, $1 \leq m < n$), fluorinated unsaturated alkyl ($C_nH_qF_{2m-q+1}$, $n=1-30$, $1 \leq m < n$, $0 \leq q \leq 2m$), alicyclic ($C_nH_{2m+1}$, $n=1-30$, $1 \leq m \leq n$), fluorinated alicyclic ($C_nH_qF_{2m-q+1}$, $n=1-30$, $1 \leq m < n$, $0 \leq q \leq 2m$), and where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus; or a modified or unmodified biomolecule (steroids, phospholipids, mono-, di- and triglycerides, mono- and polysaccharides, nucleosides, and polypeptides), where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo), or a biocompatible oligomer or polymer (polyglycolic acid);

X:

halogen (F, Cl, Br, I);

sulfonate ester (alkanesulfonates, partially or totally fluorinated alkanesulfonates, arenesulfonates, and partially or totally fluorinated arenesulfonates); or a nitrogen leaving group (diazonium ion);

or pharmaceutically acceptable salts thereof.

The generic formula for the "tail-to-tail dimeric" non-azo 1,8-naphthalimide dye is represented by Compound II, having mixtures of stereoisomers. The generic formula for the "head-to-head dimeric" non-azo 1,8-naphthalimide dye is represented by Compound III, having mixtures of stereoisomers. Similarly, the generic formula for the "head-to-tail dimeric" non-azo 1,8-naphthalimide dye is represented by Compound IV, having mixtures of stereoisomers. The different substituents and bridges for Compounds II, III and IV are:

R and R':

saturated straight-chain or branched-chain alkyl, $C_nH_{2n+1}$ ($n=1-30$);

partially or totally fluorinated saturated straight-chain or branched-chain alkyl, $C_nH_qF_{2n-q+1}$ ($n=1-30$, $0 \leq q \leq 2n$);

unsaturated straight-chain or branched-chain alkyl, $C_nH_{2m+1}$ ($n=1-30$, $1 \leq m < n$);

partially or totally fluorinated unsaturated straight-chain or branched-chain alkyl, $C_nH_qF_{2m-q+1}$ ($n=1-30$, $1 \leq m < n$, $0 \leq q \leq 2m$);

alicyclic (monocyclic or polycyclic, fused-ring, bridged-ring or spirocyclic) alkyl, $C_nH_{2m+1}$ ($n=1-30$, $1 \leq m \leq n$) with saturated or unsaturated side-chains (branched or unbranched);

partially or totally fluorinated alicyclic (monocyclic or polycyclic, fused-ring, bridged-ring or spirocyclic) alkyl, $C_nH_qF_{2m-q+1}$ ($n=1-30$, $1 \leq m < n$, $0 \leq q \leq 2m$) with saturated or unsaturated side-chains (branched or unbranched);

aryl substituted branched, unbranched or alicyclic, saturated or unsaturated alkyl, $ArC_nH_{2m+1}$ ($n=1-30$, $1 \leq m \leq n$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

partially or totally fluorinated aryl substituted branched, unbranched or alicyclic, saturated or unsaturated alkyl, $ArC_nH_qF_{2m-q+1}$ ($n=1-30$, $1 \leq m \leq n$, $0 \leq q \leq 2m$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

substituted saturated straight-chain or branched-chain alkyl, $C_nH_{2n-p+1}Y_p$ ($n=1-30$, $1 \leq p \leq 10$) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated straight-chain or branched-chain alkyl, $C_nH_qF_{2n-p-q+1}Y_p$ ($n-1-30$, $1 \leq p \leq 10$ $0 \leq q \leq 2n$);

substituted unsaturated straight-chain or branched-chain alkyl, $C_nH_{2m-p+1}Y_p$ ($n=1-30$, $1 \leq m < n$, $1 \leq p \leq 10$) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated straight-chain or branched-chain alkyl, $C_nH_qF_{2m-p-q+1}Y_p$ ($n=1-30$, $1 \leq m < n$, $1 \leq p \leq 10$, $0 \leq q \leq 2m$);

substituted alicyclic (monocyclic or polycyclic, fused-ring, bridged-ring or spirocyclic) alkyl, $C_nH_{2m+1}$ ($n=1-30$, $1 \leq m \leq n$) with saturated or unsaturated side-chains (branched or unbranched) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated alicyclic (monocyclic or polycyclic, fused-ring, bridged-ring or spirocyclic) alkyl, $C_nH_qF_{2m-p-q+1}Y_p$ ($n=1-30$, $1 \leq m < n$, $1 \leq p \leq 10$, $0 \leq q \leq 2m$) with saturated or unsaturated side-chains (branched or unbranched) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted aryl substituted branched, unbranched or alicyclic, saturated or unsaturated alkyl, $ArC_nH_{2m-p+1}Y_p$ ($n=1-30$, $1 \leq m \leq n$, $1 \leq p \leq 10$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus, and where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated aryl substituted branched, unbranched or alicyclic, saturated or unsaturated alkyl, $ArCH_qF_{2m-p-q+1}Y_p$ ($n=1-30$, $1 \leq m \leq n$, $1 \leq p \leq 10$, $0 \leq q \leq 2m$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus, and where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

a straight-chain or branched-chain group capable of complexing a metal ion, $C_nH_{2m+1}Y_q$ ($n=1-30$, $1 \leq q \leq n$, $1 \leq q \leq n/2$), where Y is O, S, Se, NH, N-R, N-Ar, PH, P-R and/or P-Ar and their acyl (including aminoacyl and peptide) derivatives, and where R is saturated alkyl ($C_nH_{2n+1}$, $n=1-30$), fluorinated saturated alkyl ($C_nH_qF_{2n-q+1}$, $n=1-30$, $0 \leq q \leq 2n$), unsaturated alkyl ($C_nH_{2m+1}$, $n=1-30$, $1 \leq m < n$), fluorinated unsaturated alkyl ($C_nH_qF_{2m-q+1}$, $n=1-30$, $1 \leq m < n$, $0 \leq q \leq 2m$), alicyclic ($C_nH_{2m+1}$, $n=1-30$, $1 \leq m \leq n$), fluorinated alicyclic ($C_nH_qF_{2m-q+1}$, $n=1-30$, $1 \leq m < n$, $0 \leq q \leq 2m$), and where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

a substituted alicyclic group capable of complexing a metal ion, $C_nH_{2m+1}Y_q$ ($n=1-30$, $1 \leq q \leq n$, $1 \leq q \leq n/2$), where Y is O, S, Se, NH, N-R, N-Ar, PH, P-R and/or P-Ar and their acyl (including aminoacyl and peptide) derivatives, and where R is saturated alkyl ($C_nH_{2n+1}$, $n=1-30$), fluorinated saturated alkyl ($C_nH_qF_{2n-q+1}$, $n=1-30$, $0 \leq q \leq 2n$), unsaturated alkyl ($C_nH_{2m+1}$, $n=1-30$, $1 \leq m < n$), fluorinated unsaturated alkyl ($C_nH_qF_{2m-q+1}$, $n=1-30$, $1 \leq m < n$, $0 \leq q \leq 2m$), alicyclic ($C_nH_{2m+1}$, $n=1-30$, $1 \leq m \leq n$), fluorinated alicyclic ($C_nH_qF_{2m-q+1}$, n=1–30, $1 \leq m < n$, $0 \leq q \leq 2m$, and where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus; or a modified or unmodified biomolecule (steroids, phospholipids, mono-, di- and triglycerides, mono- and polysaccharides, nucleosides, and polypeptides), where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo), or a biocompatible oligomer or polymer (polyglycolic acid);

X:

halogen (F, Cl, Br, I);

sulfonate ester (alkanesulfonates, partially or totally fluorinated alkanesulfonates, arenesulfonates, and partially or totally fluorinated arenesulfonates); or a nitrogen leaving group (diazonium ion);

Q:

saturated straight-chain or branched-chain alkyl, $C_nH_{2n}$ (n-1–30);

partially or totally fluorinated saturated straight-chain or branched-chain alkyl, $C_nH_qF_{2n-q}$ (n=1–30, $0 \leq q \leq 2n$);

unsaturated straight-chain or branched-chain alkyl, $C_nH_{2m}$ (n=1–30, $1 \leq m < n$);

partially or totally fluorinated unsaturated straight-chain or branched-chain alkyl, $C_nH_qF_{2m-q}$ (n=1–30, $1 \leq m < n$, $0 \leq q \leq 2m$);

alicyclic (monocyclic or polycyclic, fused-ring, bridged-ring or spirocyclic) alkyl, $C_nH_{2m}$ (n=1–30, $1 \leq m \leq n$) with saturated or unsaturated side-chains (branched or unbranched);

partially or totally fluorinated alicyclic (monocyclic or polycyclic, fused-ring, bridged-ring or spirocyclic) alkyl, $C_nH_qF_{2m-q}$ (n=1–30, $1 \leq m < n$, $0 \leq q \leq 2m$) with saturated or unsaturated side-chains (branched or unbranched);

aryl substituted branched, unbranched or alicyclic, saturated or unsaturated alkyl, $ArC_nH_{2m}$ (n=1–30, $1 \leq m \leq n$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

partially or totally fluorinated aryl substituted branched, unbranched or alicyclic, saturated or unsaturated alkyl, $ArC_nH_qF_{2m-q}$ (n=1–30, $1 \leq m \leq n$, $0 \leq q \leq 2m$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

substituted saturated straight-chain or branched chain alkyl, $C_nH_{2n-p}Y_p$ (n=1–30, $1 \leq p \leq 10$) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated straight-chain or branched-chain alkyl, $C_nH_qF_{2n-p-q}Y_p$ (n=1–30, $1 \leq p \leq 10$ $0 \leq q \leq 2n$);

substituted unsaturated straight-chain or branched-chain alkyl, $C_nH_{2m-p}Y_p$ (n=1–30, $1 \leq m < n$, $1 \leq p \leq 10$) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated straight-chain or branched-chain alkyl, $C_nH_qF_{2m-p-q}Y_p$ (n=1–30, $1 \leq m < n$, $1 \leq p \leq 10$, $0 \leq q \leq 2m$);

substituted alicyclic (monocyclic or polycyclic, fused-ring, bridged-ring or spirocyclic) alkyl, $C_nH_{2m}$ (n=1–30, $1 \leq m \leq n$) with saturated or unsaturated side-chains (branched or unbranched) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated alicyclic (monocyclic or polycyclic, fused ring, bridged-ring or spirocyclic) alkyl, $C_nH_qF_{2m-p-q}Y_p$ (n=1–30, $1 \leq m < n$, $1 \leq p \leq 10$, $0 \leq q \leq 2m$) with saturated or unsaturated side-chains (branched or unbranched) where Y is a substituted aryl group (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted aryl substituted branched, unbranched or alicyclic, saturated or unsaturated alkyl, $ArC_nH_{2m-p}Y_p$ (n=1–30, $1 \leq m \leq n$, $1 \leq p \leq 10$), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus, and where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

substituted partially or totally fluorinated aryl substituted branched, unbranched or alicyclic, saturated or unsaturated alkyl, $ArC_nH_qF_{2m-p-q}Y_p$ (n=1-30, 1≤m≤n, 1≤p≤10, 0≤q≤2m), where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus, and where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo);

a straight-chain or branched-chain group capable of complexing a metal ion, $C_nH_{2m}Y_q$ (n=1-30, 1≤q≤n, 1≤q≤n/2), where Y is O, S, Se, NH, N-R, N-Ar, PH, P-R and/or P-Ar and their acyl (including aminoacyl and peptide) derivatives, and where R is saturated alkyl ($C_nH_{2n}$, n=1-30), fluorinated saturated alkyl ($C_nH_qF_{2n-q}$, n=1-30, 0≤q≤2n), unsaturated alkyl ($C_nH_{2m}$, n=1-30, 1≤m<n), fluorinated unsaturated alkyl ($C_nH_qF_{2m-q}$, n=1-30, 1≤m<n, 0≤q≤2m), alicyclic ($C_nH_{2m}$, n=1-30, 1≤m≤n), fluorinated alicyclic ($C_nH_qF_{2m-q}$, n=1-30, 1≤m<n, 0≤q≤2m), and where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus;

a substituted alicyclic group capable of complexing a metal ion, $C_nH_{2m}Y_q$ (n=1-30, 1≤q≤n, 1≤q≤n/2), where Y is O, S, Se, NH, N-R, N-Ar, PH, P-R and/or P-Ar and their acyl (including aminoacyl and peptide) derivatives, and where R is saturated alkyl ($C_nH_{2n}$, n=1-30), fluorinated saturated alkyl ($C_nH_qF_{2n-q}$, n=1-30, 0≤q≤2n), unsaturated alkyl ($C_nH_{2m}$, n=1-30, 1≤m<n), fluorinated unsaturated alkyl ($C_nH_qF_{2m-q}$, n=1-30, 1≤m<n, 0≤q≤2m), alicyclic ($C_nH_{2m}$, n=1-30, 1≤m≤n), fluorinated alicyclic ($C_nH_qF_{2m-q}$, n=1-30, 1≤m<n, 0≤q≤2m), and where Ar is an aromatic moiety (benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole and their substituted and benzo derivatives) located either within the chain of the alkyl group or at a terminus; or a modified or unmodified biomolecule (steroids, phospholipids, mono-, di- and triglycerides, mono- and polysaccharides, nucleosides, and polypeptides), where Y is a substituted aryl group (defined above), a charged group ($CO_2^-$, $SO_3^-$, $PO_3^{2-}$, and $ROPO_2^{2-}$), a silicon derivative ($SiZ_3$, where Z is alkyl, aryl, alkoxy, aryloxy, or halo), or a boron derivative ($BZ_2$, where Z is alkyl, aryl, alkoxy, aryloxy, or halo), or a biocompatible oligomer or polymer (polyglycolic acid); or pharmaceutically acceptable salts thereof.

CHEMICAL SYNTHESES

Figure 2A:
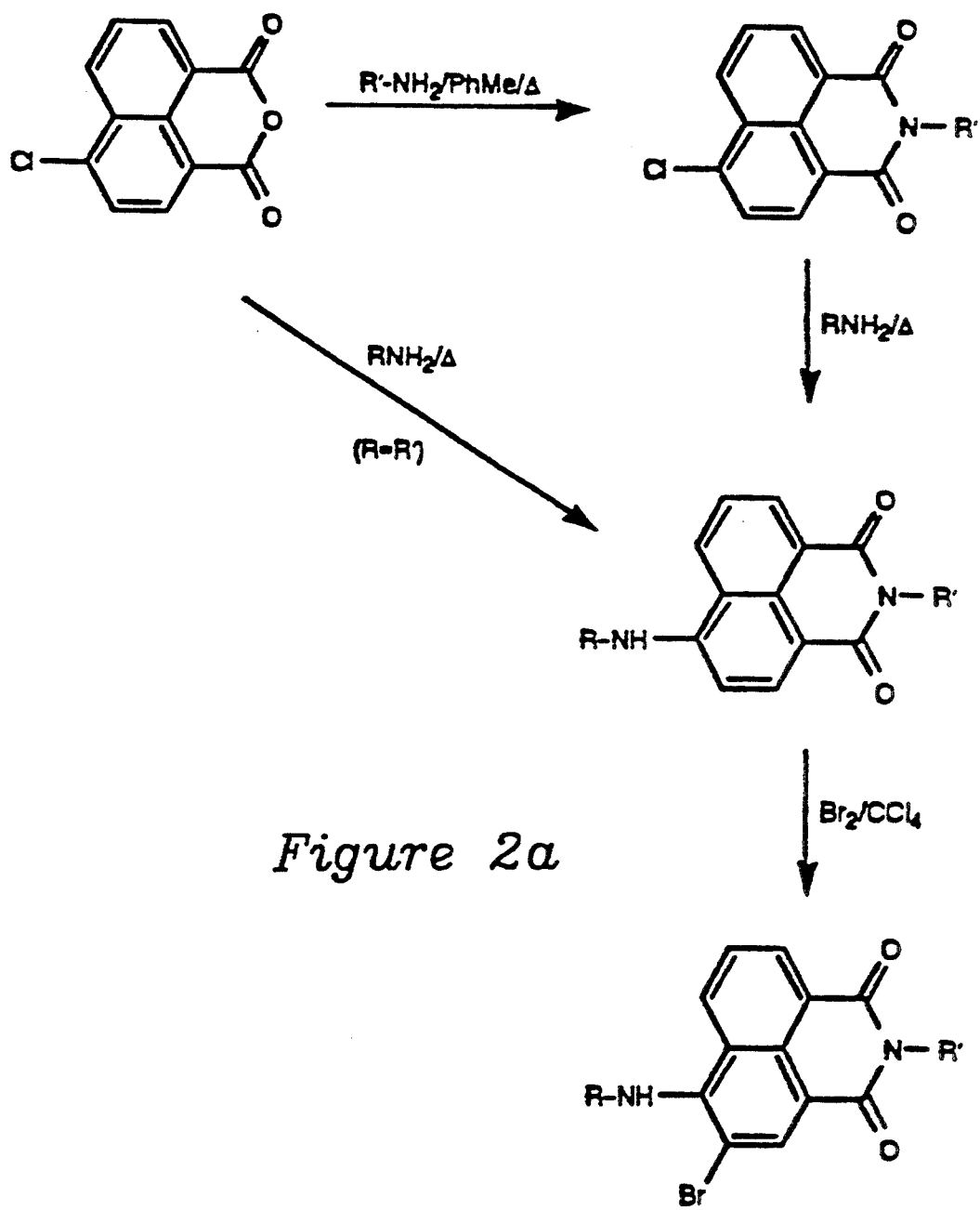
FIGS. 2 $a$ to 2 $b$ show two general reaction schemes.
Figure 2B:
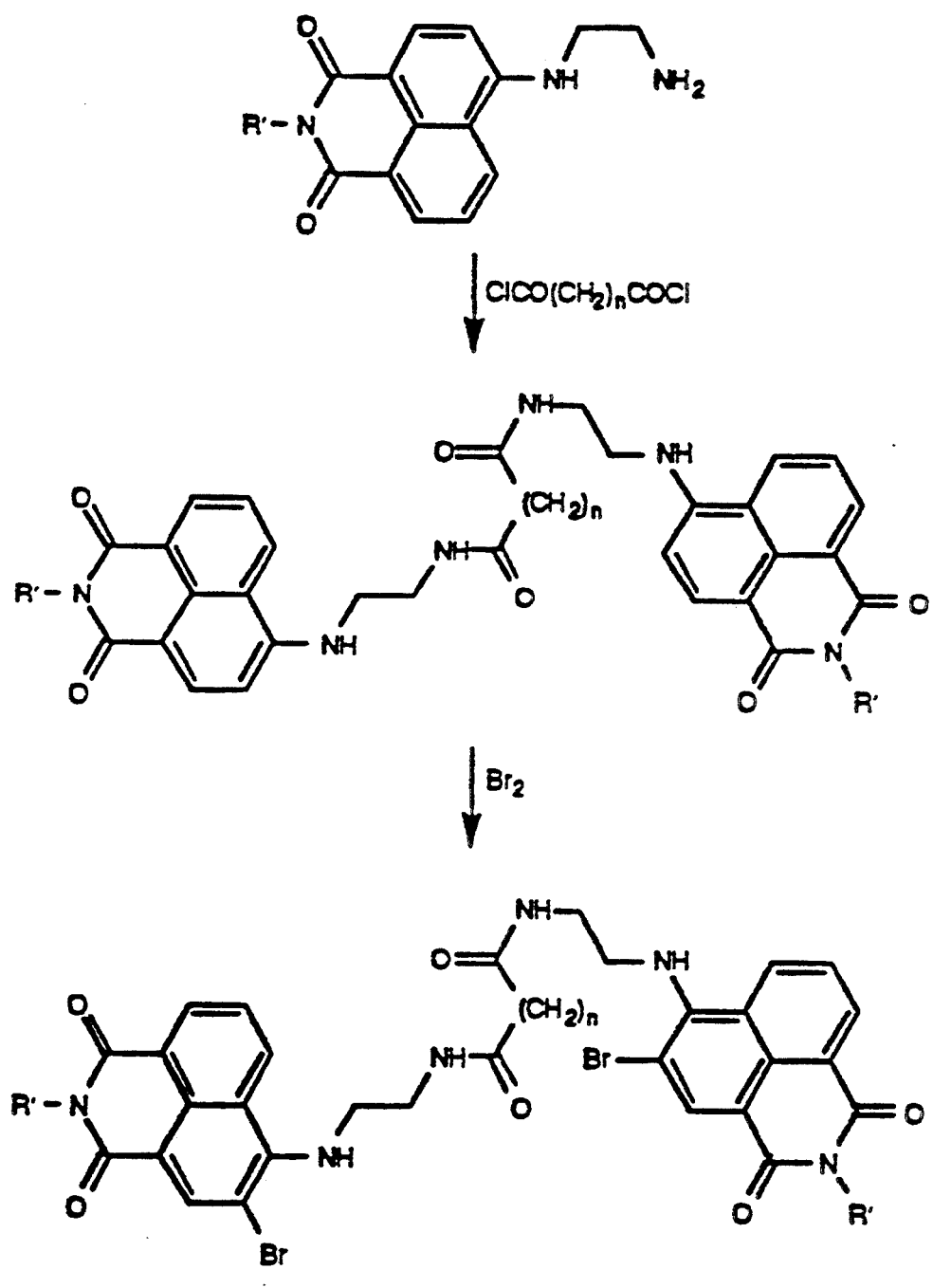

FIG. 2 illustrates some of the general reaction schemes.

I. General Procedure for Synthesis of 4-Alkylamino-N-alkyl-1,8-naphthalimides with two different alkyl groups. (I, X=H; XV, XVI, XXI, XXII, XXV, XXVI, XXVII, XXVIII, XXXIII, XXXV, XVII, XXVIII, XXIX, XL, XLI).

(a) Synthesis of the 4-chloro-N-alkyl-1,8-naphthalimide.

Recrystallized 4-chloro-1,8-naphthalic anhydride (1 equivalent.) is suspended in toluene or 1,2-dimethoxyethane (20-25 mL/g) and the primary amine (1-2 equivalent) is added. The mixture is heated to reflux, whereupon the color of the reaction mixture gradually changes from yellow to off-white. After 24 hours, the reaction mixture is cooled, and the solvent is removed by evaporation under reduced pressure. The solid residue of the 4-chloro-N-alkyl-1,8-naphthalimide is recrystallized from methanol.

Specific Example

Recrystallized 4-chloro-1,8-naphthalic anhydride (5.814 g, 25.0 mmol) was suspended in toluene (120 mL) and 1-hexylamine (3.30 mL, 25.0 mmol) was added by graduated pipette. The mixture was heated to reflux, and the color of the solution gradually changed from yellow to off-white. After 24 hours, the solids had all dissolved, and the solution was allowed to cool. The solvent was removed by evaporation under reduced pressure, and the solid residue was recrystallized from methanol to afford 4-chloro-N-hexyl-1,8-naphthalimide (LV, R=n-$C_6H_{13}$, 7.259 g, 92%) as an off-white solid. Representative compounds prepared by this method:

| R | mass of anhydride | amount of amine | solvent | yield |
|---|---|---|---|---|
| n-$C_4H_9$ | 4.185 g | 1.80 mL | toluene | 96% |
| n-$C_6H_{13}$ | 5.499 g | 3.10 mL | toluene | 90% |
| n-$C_8H_{17}$ | 4.124 g | 2.90 mL | toluene | 91% |
| n-$C_{10}H_{21}$ | 2.525 g | 2.0 mL | toluene | 70% |
| n-$C_{14}H_{29}$ | 0.536 g | 0.656 g | toluene | 95%* |
| n-$C_{16}H_{33}$ | 1.018 g | 1.071 g | toluene | 44% |
| n-$C_{18}H_{35}$ | 1.016 g | 1.480 g | toluene | 53% |
| $C_6H_5$ | 1.028 g | 42 mL | $PhNH_2$ | 70% |
| p-Br$C_6H_4$ | 1.002 g | 1.486 g | n-BuOH | 34% |

*Crude yield (b) Synthesis of the 4-alkylamino-N-alkyl-1,8-naphthalimide.

The 4-chloro-N-alkyl-1,8-naphthalimide (1 equivalent) is dissolved or suspended in the primary amine (2-20 mL/g) and the solution is heated to reflux for 18-24 hours. The resultant solution is allowed to cool, and the solvent is removed by evaporation under reduced pressure. The solid thus obtained is recrystallized from methanol. Yields are difficult to determine because of the propensity of many of these compounds to form solvates.

Specific Example

A stirred solution of 4-chloro-N-hexyl-1,8-naphthalimide (LV, R=n-$C_6H_{13}$; 10.12 g, 32 mmol) in ethylenediamine (25 mL) was heated under reflux for 18 hours. After this time, the reaction mixture was cooled to room temperature. The solution solidified, and the excess ethylenediamine was removed by evaporation under reduced pressure. The residual yellow solid was recrystallized from methanol to afford the product as yellow crystals (12.56 g).

Representative compounds prepared by this method:

| R | R' | mass of imide | volume of amine | yield |
|---|---|---|---|---|
| n-$C_4H_9$ | $CH_2CH_2NH_2$ | 0.78 g | 16 mL | 0.80 g |
| n-$C_6H_{13}$ | $CH_2CH_2NH_2$ | 1.62 g | 25 mL | 1.98 g |
| n-$C_8H_{17}$ | $CH_2CH_2NH_2$ | 1.09 g | 40 mL | 1.06 g |
| n-$C_{14}H_{29}$ | $CH_2CH_2NH_2$ | 1.113 g | 11 mL | 0.930 g |
| n-$C_{16}H_{33}$ | $CH_2CH_2NH_2$ | 0.888 g | 12 mL | 75%* |
| n-$C_{18}H_{35}$ | $CH_2CH_2NH_2$ | 0.62 g | 11.5 mL | 0.60 g |
| n-$C_6H_{13}$ | $CH_2CH_2OH$ | 1.502 g | 50 mL | 1.531 g |

*Based on unsolvated formula.

II. General Procedure for Synthesis of 4-Alkylamino-N-alkyl-1,8-naphthalimides with two identical alkyl groups. (I, X=H; V, VI, IX, X).

A stirred suspension of 4-chloro-1,8-naphthalic anhydride (1 equivalent) in the primary amine (10–30 mL/g) is heated under reflux for 18–24 hours. The resultant solution is allowed to cool to room temperature, and the amine is then removed by evaporation under reduced pressure. The crude product, which is usually an oily solid, is recrystallized from methanol.

Specific Example

Freshly recrystallized 4-chloro-1,8-naphthalic anhydride (4.32 g, 18.5 mol) was dissolved in 1-aminohexane (120 mL), and the resultant solution was heated under reflux for 18 hours. The red solution was allowed to cool, and the 1-aminohexane was removed under reduced pressure to afford the product as an oily solid. Recrystallization from methanol afforded 4-(hexyl)amino-N-hexyl-1,8-naphthalimide (I, R=R'-n-$C_6H_{13}$; 5.72 g, 81%).

Representative compounds prepared by this method:

| R and R' | mass of anhydride | amount of amine | yield | (solvent) |
|---|---|---|---|---|
| n-$C_4H_9$ | 3.106 g | 25 mL | 55% | — |
| s-$C_4H_9$ | 2.511 g | 100 mL | 79% | — |
| i-$C_4H_9$ | 2.298 g | 44 mL | 67% | — |
| n-$C_6H_{13}$ | 5.003 g | 100 mL | 61–83% | — |
| n-$C_8H_{17}$ | 5.101 g | 56 mL | 24% | — |
| n-$C_9H_{18}$ | 1.017 g | 0.8 mL | 51% | (DMF) |
| $CH_2CH_2NH_2$ | 5.100 g | 100 mL | 31% | — |
| $CH_2CH_2OH$ | 3.106 g | 25 mL | 52% | — |

III. General procedure for bromination:

The naphthalimide is dissolved in a minimum volume of carbon tetrachloride (typically 20–40 mL/g) and a slight (10 mol %) excess of bromine is added. The reaction is stirred at ambient temperature, and is monitored by thin layer chromatography. When all of the starting material has been consumed, the solvent and the excess bromine are removed by evaporation under reduced pressure. The crude product is recrystallized from methanol to afford the 3-bromo-4-(alkyl)amino-N-alkyl-1,8-naphthalimide (I, X=Br). If necessary, chromatographic purification can be carried out by column chromatography on alumina (200 g adsorbent per g of compound) eluting with chloroform-hexane mixtures.

Specific Example

To a solution of 4-(hexyl)amino-N-hexyl-1,8-naphthalimide (0.531 g, 1.40 mmol) in carbon tetrachloride (20 mL) was added bromine (0.08 mL, 1.5 mmol) by graduated pipette. The reaction mixture was allowed to stir at room temperature for 3.5 hours, and the solvent was then removed by evaporation under reduced pressure. The resultant yellow solid was recrystallized from methanol to afford 3-bromo-4-(hexyl)amino-N-hexyl-1,8-naphthalimide (VII, 0.435 g, 67%) as bright yellow needles.

Representative compounds prepared by this method:

| R | R' | mass of imide | yield |
|---|---|---|---|
| n-$C_4H_9$ | n-$C_4H_9$ | 0.407 g | 0.438 g |
| n-$C_6H_{13}$ | n-$C_6H_{13}$ | 0.531 g | 0.435 g |
| n-$C_8H_{17}$ | n-$C_8H_{17}$ | 0.584 g | 0.584 g |
| n-$C_6H_{13}$ | $CH_2CH_2NH_2$ | 0.819 g | 0.1 g* |

*Yields were low; these compounds must be prepared and purified under low-light or red-light conditions.

EVALUATION

This invention pertains to a class of predominantly hydrophobic non-azo 1,8-naphthalimide dyes whose biological and chemical activity is presumably due to a new mechanism of action termed phototautomerization-alkylation which probably proceeds in three primary steps. Step one is activation by an activating agent to generate an energetically excited species. In step two, the initially excited molecular species undergoes tautomerization to generate an alpha-haloimine which is also a gamma-halocrotonamide species. Such a species is a highly reactive alkylating agent. In step three, the active species reacts covalently with available substantially nucleophilic groups available on biological molecules such as cysteinyl, cystinyl, tryptophanyl, tyrosyl, seryl amino acid residues of peptides and proteins. Unlike many other photoactive dyes, these predominantly hydrophobic non-azo 1,8-naphthalimide dyes can be activated in an environment independent of the presence or absence of oxygen. They do not rely on the production of singlet oxygen for their mechanism of action.

This class of non-azo 1,8-naphthalimide dyes in the absence of a suitable activating agent, such as electromagnetic radiation, is substantially nontoxic to viruses, bacteria, protozoans or to other biological cells and tissues. These new dyes are readily incorporated into lipid bilayers, membranes and micelles of natural or synthetic origin. Due to the sequestration of these lipophilic dyes into hydrophobic regions of proteins, viruses, both cellular and liposomal membranes, and tissues having a high density of biomolecular nucleophilic groups, the covalent reactions initiated by the activated form of these dyes can result in chemical alteration of amino acid residues, of protein and peptide conformation and function, and can cross-link the amino acid residues, peptides, and proteins. Thus, this class of dyes can be used to kill or inactivate viral, bacterial, and protozoal infective agents, neoplastic and cancerous cells, to link desired molecular and biomolecular species to peptides, proteins, cells, and biological tissues as well as other substrates containing nucleophilic groups, and to cross-link peptides, proteins, tissues, and other substrates containing nucleophilic groups selectively upon application of an activating agent, such as electromagnetic radiation with wavelength corresponding in absorption spectrum of the dye absorption spectrum. The appropriate electromagnetic radiation absorption spectrum includes the ultraviolet through visible light to near infrared and the K-alpha, etc., X-ray absorption energies of the molecular halogen substituent. Other activating agents include thermal neutrons which could be used to activate boron-containing 1,8-naphthalimide dyes.

The partitioning of these non-azo 1,8-naphthalimide dyes into hydrophobic regions such as the interior of the lipid bilayer of liposomes and the capability of activating covalent chemical reactions with nucleophilic amino acid residues allows crosslinking of the intramembrane regions of peptides and proteins associated with the bilayer membrane selectively upon exposure to light. No crosslinking occurs until being activated by an activating agent, such as light. This is in contrast to the use of conventional dark-acting chemical cross-linking or linking agents such as formaldehyde, gluteraldehyde, succinimidyl esters, iodoactamides, or maleimides which act immediately upon contact with the appropriate protein residues during mixing by physical agitation or diffusion.

Thus, with the use of conventional dark-acting agents, it is difficult to delay initiation of the cross-linking chemical reaction until a chosen time during appropriate mixing or sequestration of mixture components. The use of the light activatable 1,8-naphthalimide dyes allows temporary delay of cross-linking until desired mixing or sequestration of liposomal membrane constituents and internalized components has been accomplished. This capability allows, for example, synthesis of liposomes containing a a completely cross-linked network of Gramacidin-D peptide units within the lipid bilayer and which contain a peptide or protein or other molecular species within the interior such as hemoglobin. The structural and functional integrity of these molecules has been maintained during the cross-linking process because the lipophilic cross-linking dye is physically isolated from the hydrophilic interior and incapable of chemical reaction with the internalized molecular species. Additionally, the lack of cross-linking in the dark by 1,8-naphthalimide dyes allows greater facility of mixing of the constituent in the dark without fear of reaction.

Light induced covalent linking of the non-azo 1,8-naphthalimide dyes with a substrate also allows their use in linking a desired biomolecular or pharmaceutical agent to target biological cells or to the surface of a biological tissue at a desired time.

Use of light activation of these dyes also allows cross-linking of proteins at different tissue surfaces in order to bond or weld biological tissues together and avoid unwanted intermediate reactions. The advantage of light induced tissue welding over thermally induced welding is less damage to tissue adjacent to the welded area due to lack of heating of surrounding tissues by diffusion during the procedure.

Strong localization of the lipophilic non-azo 1,8-naphthalimide dyes within the hydrophobic regions of enveloped or naked virus particles allows efficient killing or inactivation of the infective capability of the virus. Delay of the biological action of the dyes until activation allows temporal control during the process.

Localization of the light activated covalent reactions of the dyes with nucleophilic amino residues allows cross-linking of viral proteins between their hydrophobic regions, well away from the hydrophilic regions of these proteins which are recognized as antigenic in the generation of infective host antibodies and immunity. Thus, they are highly effective for making damaged, altered, or killed whole virus particle vaccines while preserving the outer hydrophilic exposed viral surface shapes which are important in antibody generation, and immunogenicity. Similarly, these predominantly hydrophobic non-azo 1,8-naphthalimide dyes are efficient in making damaged, altered or killed whole bacterial vaccine while preserving the immunogenicity.

Because these lipophilic dyes are both taken up by cancer cells, they offer an excellent vehicle for loading of a Boron isotope-containing compound into neoplastic cells for tumor treatment via activation with thermal neutrons.

As used herein, the word "dye" is interchangeable with the word "compound", as referred to non-azo 1,8-naphthalimides.

The term "pre-activated" as used herein denotes that the 1,8-naphthalimide dye is activated, sensitized, or excited outside the animal or human body, or outside the body tissue. Thus, the term "preactivated" denotes that the activation of the dye is accomplished away from the body tissue to be treated, away from the target tumor cells or target biological pathogenic contaminants. Hence, the activation step in the "pre-activated" method is carried out before, not after, the dye has interacted with the target tumor cells or with other pathogenic biological contaminants. In fact, the activation step in the "pre-activated" method is carried out prior to the dye being brought into contact with the tissue to be treated. There is no requirement for further activation at the target sites once the therapeutic agent has been preactivated. The pre-activated therapeutic agent so generated has a measurable and clinically useful shelf life time.

The activating agent as used herein denotes a means or an agent that is capable of activating, exciting, or sensitizing a photoactive compound. The activating agent can be radiated energy, electromagnetic energy, laser, electric current, electrons, thermal neutrons or chemicals. The electromagnetic spectrum can include visible light, xenon light, laser light, near infrared and ultraviolet light. The laser or other radiation energy can be continuous or pulsed. The pulsed energy used is such that the energy supplied has a multiple number of short pulses of relatively high energy, but at the same time, has a much lower average energy rate. The laser could be gold vapor laser, xenon arc lamp laser, argon laser, a crystal laser, a gas discharge laser, an excimer laser, krypton laser, argon ion pumped dye laser, or hollow cathode metal vapor laser, and others. Even sources such as conventional filament lamp source with appropriate filtering, an arc lamp source with appropriate filtering, or even a pulsed xenon flash lamp with appropriate filtering could be used.

The term "interact" as used herein denotes the general phenomena of having the therapeutic agent adhere to, accumulate in, or associated with the tumor cells or other pathogenic biological contaminants infecting a body tissue.

The term "pathogenic biological contaminants" is to be understood to include: viruses, enveloped or not enveloped; microorganisms; parasites; bacteria and the like.

"Tumors" or "tumor cells" is understood to encompass malignant and non-malignant types and include, among others: cancer of the bone and connective tissues; cancer of the eyes; leukemias; lymphomas; myelomas; melanomas, breast cancer, lung cancer, ovarian cancer as well as other types of cancer and solid tumors.

The term "body tissue" as used herein is to be understood to include "body fluid," red blood cells, white blood cells, platelets, cryo precipitate from blood plasma, other plasma proteins, bone marrow, skin, cornea, ligament, tendon and other tissues from an animal or a human.

The term "body fluid" as used herein is to be understood to include whole blood, any formed elements of the blood, blood plasma, serum, fluids containing such components, fluids from plasmapheresis, plasma fibrinogen, cryo-poor plasma, albumin, gamma globulins, semen, and other fluids introduced or intravenously injected into the body of a patient or an animal using known administration techniques. The term "body fluid" is to be understood to include body fluid prior to, or after, physical as well as chemical fractionation, separation or freezing.

The term "external" as used herein is to denote outside the animal or human body.

The term "animal" as used herein is to denote any warm-blooded animal; this includes human and other domestic and farm animals.

The term "carrier" as used herein denotes a vehicle, a solution containing water, buffers, serum, serum proteins, lipoproteins, artificial bio-membranes, micelles, liposomes, monoclonal antibodies, carbohydrates, cyclodextrans, organic solvents or other pharmaceutically acceptable, or compatible, solutions. The carrier, or vehicle, used is pharmaceutically compatible in that it is relatively non-toxic to the normal cells and normal tissues and it does not react with the solute or therapeutic agent contained therein.

The phrase "effective amount" as used herein is to denote the concentration or level of the therapeutic agent that can attain a particular end, such as cross-linking, a cure or a destruction of the undesirable cells, such as tumor cells, or pathogenic biological contaminants, without producing pronounced toxic symptoms.

SYNTHETIC MEMBRANE SYSTEMS

The behavior of the dyes of the present invention has been studied in synthetic vesicles, prepared by standard protocols of ethanol injection or sonication, and micelles for two major reasons: Firstly, the vesicle system is easier to control and simpler to understand than a biological system with its full complement of proteins and its full range of lipid components. Secondly, many of the potential applications discussed above are based upon lipid bilayer or micelle technology. The descriptions below refer to explicit cases to aid in evaluation of the invention.

(1) Binding Kinetics

All of the vesicles used in these studies were prepared to have a final lipid, egg lecithin+cholesterol concentration of 10 mg/ml. Cholesterol concentrations were varied between 0 and 45 mol % by varying the lipid composition from which the vesicles were produced. The subject dyes were added in 10% aqueous isopropyl alcohol solutions to vesicle suspensions in water. The dyes are non-fluorescent in 10% aqueous isopropyl alcohol, but are highly fluorescent in vesicles. The increase in fluorescence was monitored at an excitation wavelength of 460 nm and an emission wavelength of 519 nm. Fluorescence intensity was measured as a function of time, and fit to a standard first-order kinetic plot. Compound 1b is Compound I, wherein $R=R^1=$n-hexyl and $X=H$. The rate constants are given in Table 1.

TABLE 1

Rate Constants for Binding of Compound VII to Synthetic Vesicles of $\beta$-Oleyl-$\gamma$-stearoylphospahtidyl Choline

| mol % cholesterol | rate constant ($s^{-1}$) |
|---|---|
| 0 | $0.814 \pm 0.005 \times 10^{-3}$ |
| 15 | $1.020 \pm 0.005 \times 10^{-3}$ |
| 30 | $1.54 \pm 0.02 \times 10^{-3}$ |
| 45 | $2.75 \pm 0.01 \times 10^{-3}$ |

(2) Bleaching Kinetics

The dye was incorporated into synthetic vesicles as described above. The vesicles were irradiated with a 150-W Oriel xenon arc lamp at a distance of 4 cm from the lens at a thermostated temperature of 20° C. The change in fluorescence intensity with time was determined above, and the results plotted as a standard first order plot. The results are given in Table 2.

TABLE 2

Rate Constants for Bleaching of Compound VII in 31 Synthetic Vesicles of $\beta$-Oleyl-$\gamma$-stearoylphospahtidyl Choline

| mol % cholesterol | rate constant ($s^{-1}$) |
|---|---|
| 0 | $1.08 \pm 0.08 \times 10^{-3}$ |
| 15 | $2.00 \pm 0.13 \times 10^{-3}$ |
| 30 | $3.08 \pm 0.20 \times 10^{-3}$ |
| 45 | $3.1 \pm 0.9 \times 10^{-3}$ |

Synthetic vesicles of $\beta$, $\gamma$-distearoylphosphatidyl choline containing Compound VII do not bleach, and show only very slow photodegradation of the dye.

(3) Effect of Irradiation on Lipid Structure

Upon irradiation, crude phospholipid vesicles containing Compound VII give rise to new lipids whose t.l.c. mobility is lower than the starting phospholipid mixture, indicating probable cross-linking.

(4) Effects of Irradiation on Membrane-Bound Protein Function

Cytochrome c, a mitochondrial protein which is peripherally associated with membranes was studied as a model for the effect of photomodification of the membrane lipids on protein function. At pH 7.5 and 0° C., the rate of oxidation of vesicle-bound cytochrome c $(7 \times 10^{-6}$ M) by $CO(phen)_3{}^{3+}$was $25 \pm 1$ $s^{-1}$. Upon addition of Compound VII ($1 \times 10^{-7}$ M) to the vesicles containing reduced cytochrome c, and subsequent irradiation as described above, the rate constant for oxidation of the bound cytochrome c under the same conditions was reduced to $2 \pm 1$ $s^{-1}$.

BIOLOGICAL STUDIES

The behavior of the subject dyes in living systems has been explored using a variety of cells and media, as well as viruses. Binding and light-kill studies have been carried out using H9 cells, a transformed immortalized T-lymphoma, and Daudi cells as representative mammalian cells.

(1) Uptake Into Living Cells

The staining of cells with Compound VII or Compound 1b was effected using the following protocol: H9 cells were counted using a hemocytometer. $1.25 \times 10^7$ cells at $600 \times g$. The pellet was resuspended in 25 ml of fresh, prewarmed RPMI-1640+10% FCS (this gives $5 \times 10^5$ cells/ml). The suspension was divided into 3 aliquots of 7 ml each, and Compound 1b (5 mg/ml in 2-propanol) was added to give solutions of 1, 5 and 25 μM. The solutions were maintained at a constant temperature, and samples (1 ml) were taken at time 0, 0.5, 1, 2, 3, and 7.5 hours, and centrifuged at $500 \times g$ for 30 s, resuspended in 1 ml fresh RPMI-1640+10% FCS, and centrifuged again. For measurement, the pellet was diluted in 3 ml PBS+0.1% CTAB immediately prior to fluorescence measurement. Fluorescence measurements were made using an excitation wavelength of 451 nm, and an emission wavelength of 526 nm. The results are plotted as a standard first-order kinetic plot and given in Tables 3 and 4.

TABLE 3

Rate Constants for Uptake of Compound 1b by H9 Cells in 10% Fetal Calf Serum at 37° C.

| cpd. concentration (μM) | rate constant ($s^{-1}$) |
|---|---|
| 1 | $3.6 \pm 1.7 \times 10^{-4}$ |
| 5 | $3.3 \pm 0.7 \times 10^{-4}$ |
| 25 | $2.5 \pm 0.3 \times 10^{-4}$ |

TABLE 4

Rate Constants for Uptake of Compound 1b by H9 Cells in 10% Fetal Calf Serum at 4° C.

| cpd. concentration (μM) | rate constant ($s^{-1}$) |
|---|---|
| 1 | $3.5 \pm 0.6 \times 10^{-4}$ |
| 5 | $2.7 \pm 1.0 \times 10^{-4}$ |
| 25 | $2.3 \pm 0.9 \times 10^{-4}$ |

Experiments on the effects of temperature and the presence of colchicine are summarized as: The total uptake of Compound 1b was decreased in the presence of colchicine. The slope of the log/log plot of fluorescence vs. time shows essentially the same slope after 2 hours in the presence and absence of colchicine; this supports the view that both passive diffusion across the lipid plasma membrane (rate unaffected by colchicine) plus pinocytosis (poisoned by colchicine), contribute to takeup of Compound 1b. The protocol used is as above in (1), modified as below for those experiments in the presence of colchicine: Colchicine (1 mg/ml) was added to H9 cells at $5 \times 10^5$ cells/ml, and incubated for 1 hour. The cells were centrifuged, fresh medium was added, and 1b (25 μM) was added. Samples were taken at 0, 2, and 4 hours.

(2) Location Into Living Cells

Following the protocol of (1), above, H9 cells were stained with Compound 1b, and the technique of fluorescent microscopy was used to determine visually the sites of localization of dye fluorescence in living cells. Specifically, H9 cells were counted with a hemocytometer and diluted to $5 \times 10^5$/ml. Compound 1b was added to two aliquots to give dye concentrations of 5 and 25 μM, and the tubes were incubated for 1.5 hours. Cytospin slides of the cell suspensions were made and they were examined with the fluorescence microscope (Olympus AH-2) using B excitation plus a 460 nm interference excitation filter and a 495 nm emission filter. The cells were also counted with a hemocytometer and their viability determined (see below). Both samples containing Compound 1b were highly fluorescent with the cytoplasm being the primary site. The control slide showed no fluorescence at all. The cytoplasm displayed a veil-like pale green fluorescence plus bright yellow-green punctate sites of fluorescence. The former may reflect the diffusional component of the dye incorporation, or may reflect binding in the ER membrane. The latter may indicate lysosomal localization of pinocytosed dye as occurs with Lucifer Yellow. The Compound 1b was rigorously excluded from the cell nucleus.

(3) Cell Viability in Absence of Light

Cell viability was determined using dye incorporated according to the protocol directly above. Viability was determined using a trypan blue dye exclusion test in which "live" cells with competent cell membranes exclude the dye. Table 5 summarizes the data obtained using cells exposed to Compound 1b in culture medium, and Table 6 summarizes data obtained using cells exposed to Compound VII.

TABLE 5

Viability of H9 Cells Following Dark Exposure to Compound 1b*

| (μM) cpd. 1b | live cells | dead cells | % viability |
|---|---|---|---|
| 0 | 136 | 2 | 98.6 |
| 5 | 116 | 4 | 96.7 |
| 25 | 136 | 4 | 97.1 |

*Viability determined 2.5 hours after completion of exposure to dye in medium for 1.5 hours.

TABLE 6

Viability of H9 Cells Following Dark Exposure to Compound VII

| cpd. VII (μM) | live cells | dead cells | % viability |
|---|---|---|---|
| Viability determined 1 hour after completion of exposure to compound in 100% human plasma for 4 hours. | | | |
| 1 | 280 | 12 | 95.9 |
| 5 | 286 | 16 | 94.7 |
| 25 | 339 | 16 | 95.5 |
| Viability determined 1 hour after completion of exposure to compound in medium for 24 hours | | | |
| 0 | 139 | 18 | 88.5 |
| 1 | 151 | 23 | 86.8 |
| 10 | 104 | 26 | 80.0 |
| 25 | 148 | 38 | 79.6 |
| 50 | 124 | 128 | 42.5 |

The results given in Tables 5 and 6 show that the dyes exhibit little dark toxicity in either the low or high protein and lipoprotein concentrations of medium of whole human plasma, respectively.

(4) Dye-Mediated Light Kill of Living Cells

Photoinduced killing of H9 cells with Compound 1b as the mediator of photochemical toxicity were carried out according to the following protocol:

Compound 1b was added to the H9 cells (5×10⁵/ml) in medium, or 100% human plasma to give dye concentrations of 0, 25 and 100 μM (1 control, 2 duplicates of both non-azo dye samples). Two 2-ml aliquots of each of the duplicated dye samples was irradiated with 10 J/cm² total energy of 450±35 nm wavelength light in a sealed 3-ml test tube. Immediately after irradiation, the cells were centrifuged at 450×g for 10 minutes, and the pellets resuspended in the original volume of fresh RPMI-1640+10% FCS+gentamycin. The cell suspensions were transferred to a 12-well TC plate and placed in a 37° C. 5% $CO_2$ incubator. Cell viability counts (trypan blue) were carried out at 4, 24, 48, and 72 hours post irradiation. The results of these experiments are summarized in Tables 7 (medium) and 8 (100% human plasma).

TABLE 7

Photoinduced Kill of H9 Cells Mediated By Compound 1b in 10% FCS Medium Percent Viability

| Cpd. conc. (μM) | 0 | 25 | | 100 | |
|---|---|---|---|---|---|
| Time | no hv | no hv | hv | no hv | hv |
| 4 | 97.8 | 96.9 | 62.8 | 94.6 | 87.2 |
| 24 | 96.4 | 94.8 | 8.4 | 94.6 | 52.0 |
| 48 | 91.5 | 90.5 | 10.0 | 91.3 | 64.8 |
| 72 | 86.3 | 91.4 | 30.6 | 85.1 | 71.4 |

TABLE 8

Photoinduced Kill of H9 Cells Mediated by Compound 1b in 100% Human Plasma Percent Viability

| Cpd. conc. (μM) | 0 | 25 | | 100 | |
|---|---|---|---|---|---|
| Time | no hv | no hv | hv | no hv | hv |
| 4 | 100 | 97.2 | 97.9 | 99.2 | 97.4 |
| 24 | 97.0 | 93.4 | 94.4 | 94.3 | 92.4 |
| 48 | 91.9 | 86.4 | 86.5 | 90.7 | 92.6 |
| 72 | 81.3 | 85.0 | 90.2 | 87.4 | 88.2 |

Photoinduced killing of H9 cells with Compound VII as the mediator of photochemical toxicity were carried out in 10% FCS medium according to the same general protocol using concentrations of the dye at 0, 5, 25 and 100μM., and irradiating at 420±5 nm at 10 J/cm² total energy. The results of viability studies determined 4 hours after the procedure are given in Table 9.

TABLE 9

Photoinduced Kill of H9 Cells Mediated by Compound VII in 10% FCS Medium Percent Viability

| Cpd. conc. (μM) | 0 | 5 | 25 | 100* |
|---|---|---|---|---|
| no hv | 85.7 | 86.5 | 90.0 | — |
| hv | 88.2 | 0.0 | 0.0 | 1.8 |

*Note:
The light from the filter was only able to reach approximately 2 mm into the 100 μM irradiated sample due to absorption.

An additional study using DAUDI cells and lower concentrations of Compound VII was performed according to the same protocol for studying the photochemical kill of H9 cells mediated by Compound VII. Viability was determined by the trypan blue assay above, as well as by [³H]-thymidine incorporation. The [³H]-thymidine incorporation protocol was as follows:

After irradiation, the cells were diluted to 3×10⁵ cells/ml with medium containing twice the normal concentration of gentamycin. The cells were pipetted into a 96-well TC plat (100 μl/well) and incubated at 37° C. in a 5% $CO_2$ incubator for 36 hours. At this time 1 μCi of [³H]-thymidine was added and allowed to incorporate for 6 hours. The cells were then harvested on glass fiber filters and placed into scintillation vials to which cocktail was added. The samples were counted on a Beckman model LS 6000IC scintillation counter. The results are summarized in Table 10.

TABLE 10

Photoinduced Cell Kill of DAUDI Cells Mediated by Compound VII in 10% FCS Medium CPM

| Cpd. conc. (μM) | no hv | hv |
|---|---|---|
| 0 | 5.3 ± 0.2 × 10⁴ | 2.5 ± 0.1 × 10⁴ |
| 1 | 5.1 ± 0.3 × 10⁴ | 1.2 ± 0.4 × 10² |
| 5 | 4.8 ± 0.3 × 10⁴ | 1.1 ± 0.3 × 10² |
| 10 | 4.5 ± 0.2 × 10⁴ | 1.0 ± 0.4 × 10² | inactivator at concentrations as low as 1 μM. using light energy fluxes in the range of 10 J/cm².

(5) Encapsulation of Hemoglobin

Bovine hemoglobin was purified by the addition of 3 volumes of deionized water to bovine blood obtained from a local slaughter house followed by gentle agitation for one hour. Cell debris was removed by centrifugation at 18,000×g for 15 minutes. No further purification of the hemoglobin was attempted for these studies. This hemoglobin solution was warmed to 40° C. on a stirring hotplate and 0.10 volume of lipid/dye solution slowly injected into the hemoglobin solution through a septum on an inverted flask. The lipid/dye solution consisted of 10 mg lecithin, 2 mg gramicidin, and 1 ml of 1.1 mg/ml dye dissolved in Cremophor RH 40 all dissolved in ethanol. Sonication was used to suspend all lipid. After the solution had cooled to room temperature, the vesicles were dialyzed overnight against 0.325M Tris-Cl⁻pH 8.0. Free hemoglobin was removed from the liposomes by gel filtration over G-50 and subsequent passage over an A-25 anion exchange column equilibrated with 32 mm Tris-Cl⁻pH 8.5. All manipulations were performed under fluorescent lighting. Further exposure to light from a Xenon arc lamp did not increase the stability of the preparation. Vesicle samples were lyophilized and subsequently resuspended in deionized water.

(6) Effect of Compound VII on Viruses

Human Herpes Simplex Virus Type I (HSV-I). Cell-free and serum-free HSV-I were suspended in Liebowitz medium at nominal PFU values of 5×10⁵/ml. Compound VII was dissolved in chremophor to give a 20 μM stock solution, and aliquots of the dye stock solution were dissolved in viral suspensions to give dye concentrations varying between 78 nM and 10 μM. One-ml aliquots of viral suspension containing Compound VII were placed in 35 mm diameter Petri dishes and irradiated with 420±5 nm light filtered from a xenon arc lamp for 9 min 10 sec to give 20 J/cm² light energy flux. Standard plaque assay for vial infectivity gave survival data tabulated in Table 11, below (% survival=[infectivity of irradiated virus/infectivity of dark control]).

TABLE 11

Photoinduced Viral Inactivation Mediated by Compound 1a Infectivity

| Cpd. conc. (μM) | PFU/ ml | PFU/ ml | Average | % Survival | log₁₀ reduction |
|---|---|---|---|---|---|
| 0 (control) | 5.5 × 10⁵ | 7.0 × 10⁵ | 6.25 × 10⁵ | | |

TABLE 11-continued

Photoinduced Viral Inactivation Mediated by Compound 1a
Infectivity

| Cpd. conc. ($\mu M$) | PFU/ ml | PFU/ ml | Average | % Survival | $\log_{10}$ reduction |
|---|---|---|---|---|---|
| 10 | 0 | 0 | 0 | <0.0002 | >5.7 |
| 5 | 0 | 0 | 0 | <0.0002 | >5.7 |
| 2.5 | 0 | 0 | 0 | <0.0002 | >5.7 |
| 1.25 | 0 | 0 | 0 | <0.0002 | >5.7 |
| 0.625 | 0 | — | 0 | <0.0002 | >5.7 |
| 0.312 | 10 | 5 | 7.5 | 0.0012 | 4.9 |
| 0.156 | 20 | 15 | 17.5 | 0.0028 | 4.5 |
| 0.078 | 45 | 30 | 37.5 | 0.006 | 4.2 |

Bovine Herpes Virus Type I (BHV-1). Cell-free and sere-free virus (BHV-1 reference strain from Dr. M. L. Vickers, ADL SDSU) was purified by potassium tartrate gradient ultracentrifugation. Virus was then resuspended in minimal buffer. Compound VII was diluted with ethanol to a concentration of 5 mg/ml. The dye stock solution was prepared by sequentially adding the ethanolic dye solution to fetal bovine serum (FBS), and diluting the dye-FBS mixture with MEM to give 10% FBS in MEM, so that the final concentration of the compound was 500 ng/ml. All dilutions of the dye in the medium were made from this stock solution. Dye/-virus mixtures were all prepared as 1:1 mixtures of virus and dye stock solution. The virus was incubated for 30 min at 37° C. prior to irradiation, and then irradiated using a xenon arc lamp to give 10 J/cm$^2$ total irradiative flux. Photomodified virus was then incubated with the appropriate cells (fetal bovine lung-FBL-or MDBK) in 10% FBS in MEM for 1 hour. Then unbound virus was taken off, the cells were washed with Ca/Mg-free PBS, and the cells were then placed in 10% FBS-MEM. The cells were incubated for 24 hours at 37° C. in a 5% CO$_2$ incubator. After 24 and 48 hours, the cells were assayed for cytopathic effects (CPE), and the results expressed in terms of using TCID$_{50}$ units. The viral inactivation data are expressed in terms of % inactivation in Table 12.

TABLE 12

Photoinactivation of Bovine Herpes Virus Type I
Mediated by Compound VII
% Inactivation

| Cpd. conc. ($\mu M$) | 24 h | $\log_{10}$ red. | 48 h | $\log_{10}$ red. |
|---|---|---|---|---|
| 0 | 0 | | 0 | |
| 0.035 | 99.4 | 3.2 | 89.9 | 0.95 |
| 0.070 | 99.8 | 3.7 | 98.7 | 2.0 |
| 0.14 | >99.98 | >3.7 | 99.4 | 3.2 |
| 0.27 | >99.98 | >3.7 | 99.4 | 3.2 |
| 0.54 | >99.98 | >3.7 | >99.98 | >3.7 |
| 1.09 | >99.98 | >3.7 | >99.98 | >3.7 |

Surface Antigen Assays. The BHV-1 virus prepared as above (20480 TCID$_{50}$) was (i) held as control; (ii) treated with dye (concentrations from 7.5 to 250 ng/ml) in cell culture medium; or (iii) treated with Compound VII and light-treated in cell culture medium. All virus was plated in 96-well flat bottom plates for 24 hours in 5x replicates on FBL cells. At that time the wells were examined for CPE, scored, and 2x wells were fixed in acetone and paraformaldehyde for examination of intracellular and surface BHV-1 antigen, respectively. The cells were treated with 50 $\mu$l of an anti-BHV-1 monoclonal antibody (gift of Dr. J. Collins, Diagnostic Laboratory, Colorado State University, School of Veterinary Medicine) used as a common diagnostic reagent, for 30 minutes at room temperature. The cells were further stained with either FITC-labeled anti-mouse or biotinylated anti-mouse and avidin rPE. The samples were placed on slides and read by fluorescent microscopy using a 495 nm excitor filter and 525 long pass emission filter on a Leitz epifluorescent microscope. The results were as follows:

Control virus—Both surface and internalized viral antigen was observed in the infected cells and most cells had clearly demonstrable internal antigen.

Virus and dye (dark control)—Much surface viral antigen was detected at all dye concentrations. An interesting observation was that when the rPE was used, an intermediate color to the probe red and the yellow-green of Compound VII was observed, as if FET was occurring. Internal antigen was observed and correlated with CPE levels. Cells fixed with acetone allowed for examination of the viral antigen, but the fixation removed the Compound VII.

Photochemically attenuated virus—The results were similar to the dark control. Surface antigen was observed at all concentrations of Compound VII, and internal antigen was observed at all concentrations of Compound VII which showed CPE. The same color effect was seen in paraformaldehyde fixed cells.

(7) Effect Of Ed6Br (Compound VII) And Light On Aqueous Suspensions Of Herpes Simplex Virus Type 1

Herpes simplex virus type 1 (HSV-1), the MacIntyre strain, was purchased from the American Type Culture Collection (ATCC) and propagated in Vero cells (ATCC) to a concentration of $10^6$–$10^7$ plaque forming units (PFU) per milliliter (ml). This solution was used as stock virus. A volume of 0.1–0.5 ml of stock virus was added to separate aliquots of modified Leibowitz medium (L$_{15}$ medium, Whittaker MA Bioproducts, and containing 2.5% or less of serum proteins) in order to give a PFU concentration between $10^5$ and $10^7$.

Ed6Br in Cremaphor EL (approximately 2.5 millimolar) was added to duplicate tubes of the virus-medium mixture. The concentrations of Ed6Br employed were 0.78, 0.156, 0.312, 0.625, 1.25, 2.5, 5.0 and 10.0 micromolar. Duplicate tubes representing each concentration of Ed6Br in the medium-virus mixture were irradiated by light at a wave length of approximately 420 nm with a fluence of about 20 J/cm$^2$. Approximately 30–60 min. elapsed between the addition of each concentration of Ed6Br and exposure to light. During the holding period, the samples were maintained at 4° C. Except during the time of irradiation, all manipulations were carried out with minimal exposure to extraneous light. A sample of virus-medium mixture but not containing Ed6Br was also irradiated under the same conditions. During the holding period and the period of irradiation, the duplicate samples of virus and medium containing different concentrations of Ed6Br were held in the dark. In addition, samples of the three different samples containing different concentrations of Ed6Br and a sample of the virus-medium mixture without Ed6Br were also maintained in the dark.

Each sample including the stock virus were assayed on Vero cells for PFU/ml of HSV-1. The assay consisted of growing Vero cells in minimal essential medium with Hanks balanced salt solution supplemented with 10% fetal bovine serum, L-glutamine and antibiotics. Hepes buffer (2%) was added for growth in open plates (twelve well microplates from CO-star). Ten fold dilutions of each sample were prepared and 0.1 ml of the appropriate dilution for each individual sample was adsorbed at 37° C. for 1.5 hr. on a cell monolayer from which the growth medium had been removed. After the adsorption period, the cell monolayer was washed and an overlay consisting of equal volumes of 2X strength L-15 medium and 2% methylcellulose was added. Following an appropriate incubation time at 37° C. (about 4 days), the overlay medium was removed. Monolayers were fixed with methanol and stained with giemsa to elaborate the presence of plaques. The plaques were counted using a dissecting microscope at a magnification of 20X.

The results of the experiment can be observed in Table 13. It is clear that Ed6Br in a concentration as low as 0.078 mM, in combination with light at a wavelength of 420 #5 nm having an energy density of 20 J/cm2, achieved a near total (larger than 99.99%) kill of HSV-1 in aqueous medium containing 2.5% or less of serum proteins. The use of larger amounts of Ed6Br resulted in a similar reduction in viral infectivity. Vital-medium suspension samples containing the 8 different concentrations but which were not irradiated showed no evidence of cellular toxicity when assayed in the Vero cells as described above.

TABLE 13

Inactivation of HSV-1 with Ed6Br (in Cremophor) and 20 J/cm2 of Light at 420 nm

| Sample | Irradiation | PFU/ml | $Log_{10}$ Reduction |
|---|---|---|---|
| HSV Control | Yes | $6.3 \times 10^5$ | |
| HSV + 10 μM Ed6Br | Yes | 0 | 5.799 |
| HSV + 5 μM Ed6Br | Yes | 0 | 5.799 |
| HSV + 2.5 μM Ed6Br | Yes | 0 | 5.799 |
| HSV + 1.25 μM Ed6Br | Yes | 0 | 5.799 |
| HSV + .625 μM Ed6Br | Yes | 0 | 5.799 |
| HSV + .312 μM Ed6Br | Yes | $7.5 \times 10^0$ | 4.924 |
| HSV + .156 μM Ed6Br | Yes | $1.8 \times 10^1$ | 4.544 |
| HSV + .078 μM Ed6Br | Yes | $3.8 \times 10^1$ | 4.219 |

PFU: Plaque forming unit.
HSV-1: Diluted 1:10 in medium yielded $6.0 \times 10^5$ PFU/ml.
Virus diluted in blood and not irradiated yielded $6.3 \times 10^5$ PFU/ml.

(8) Protein Cross-Linking With DiEd6Br (Compound XLIV) And Light

Gel electrophoresis studies of various individual protein preparations containing DiEd6Br have demonstrated the formation of slower electromigrating, thus heavier, molecular species upon photoirradiation of solutions containing both protein and the dye with light of nominally 420 nm wavelength and the complete absence of these species in like protein sample controls with or without DiEd6Br in the absence of light. Additional control with photoillumination showed absence of the heavier species in the absence of DiEd6Br. Concomitant with the appearance of the heavier species with photoillumination with the decrease in intensity of electromigrated bands of the initially present protein. Additionally, comparison of molecular weights of the newly appearing species deduced from electromigration distance showed the new bands to have molecular weights closely approximating integral multiple values (e.g., 2X, 3X, 4X, . . . ) of the value for the parent basic structural protein unit; e.g., monomer. This approximately integral multiple molecular weight relationship of the initial protein monomers and the heavier species formed upon photoillumination strongly suggested the crosslinking of two or more protein monomers by DiEd6Br upon reaction of each terminal naphthalamide moiety in the metastable states with nucleophilic residues of the pairwise linked proteins.

Results of experiments demonstrating crosslinking of proteins in the presence of DiEd6Br upon photoillumination with filtered light of 420 #5 nm wavelength are summarized in Table 14. In these experiments, the lipophilic DiEd6Br was introduced into the aqueous suspensions of the proteins through the use of Cremophor EL micelles. During equilibration prior to light exposure, the photochemical transferred to the hydrophobic environments of the viral envelope of vesicular stomatitis virus (VSV) and lipid intenor of high density lipoprotein (HI)L) via collisional contact with the dye bearing micelles and via similar collision to the more hydrophobic surface regions of the proteins of F-actin polymers and albumin dissolved in aqueous solution.

TABLE 14

Protein Crosslinking with DiED6Br

Part A: Results

| Systems | Protein Mononomers | Gel mw (kD) | Inferred Crosslinked Species | Gel mw (kD) |
|---|---|---|---|---|

1. Hydrophobic-lipid membrane with DiEd6Br delivered in Cremophor EL (ethoxylated caster bean oil) micellar suspensions.

| | | | | |
|---|---|---|---|---|
| (a) Human High Density Lipoprotein (HDL) | Apoprotein I | 17.8 | 8 Apo-protein I units | 141 |
| (b) Vesicular stomatitis Virus (Ogden) strain) (VSV) | G-protein (envelope glyco-protein) | 63 (incl. carbo-hydrate moeity) | 2 G-protein units or 1 G-protein + 1 M-protein units | 130 |

Plus many ill separated heavier bands merging together near origin.

2. Hydrophobic regions within proteins with DiEd6Br delivered in Cremophor EL (ethoxylated castor bean oil) micellar suspension.

| | | | | |
|---|---|---|---|---|
| (a) F-actin polymers of G-actin in 100 nM KCl | G-actin monomers | 47 | 2 G-actin monomers | 94 |
| | | | 3 G-actin monomers | 141 |

Plus many ill separated heavier bands merging together near origin.

| | | | | |
|---|---|---|---|---|
| (b) Human serum Albumen (HSA) in Phosphate buffered saline pH = 7.2 | HSA monomer | 64 | 2 HSA units | 120 |
| | | | 3 HSA units | 180 |
| | | | 3 HSA units | 240 |

Plus many ill separated heavier bands merging together near origin.

Part B: Methods Summary

| System | Concentration Protein | DiEd6Br | Fluence[3] | Gel System[4] |
|---|---|---|---|---|

1. Hydrophobic-lipid membrane

| | | | | |
|---|---|---|---|---|
| (a) Human High Density Lipoprotein (HDL) | 10 mg/ml[1] | 25.0 μM | 400 J/cm² | SDS-PAGE |
| (b) Vesicular Stomatitis Virus (VSV) | 300–400 μg/ml (approximately 1.5 μM in both G and M proteins) | 10.0 μM | 460 J/cm² | SDS-PAGE |

2. Hydrophobic Protein Regions

| | | | | |
|---|---|---|---|---|
| (a) F-actin | 85.7 μM[2] | 40.0 μM | 400 J/cm² | SDS-PAGE |
| (b) Human | 60.0 μM | 30.0 μM | 791 J/cm² | SDS- |

TABLE 14-continued

Protein Crosslinking with DiED6Br

| Serum Albumen | Page |
|---|---|

[1] Total HDL concentration.
[2] G-actin monomer concentration.
[3] 420 ± 5 nm wavelengths filtered from 2 xeonon arc lamps at an irradiance of 20 mW/cm2.
[4] Proteins were dissolved in sodium dodecyl sulfate (SDS) and electrophoresed on polyacrylamide gradient gels (7–11%) and stained with silver.

(9) Effect Of DiEd6Br (Compound XLIV) And Light On Aqueous Suspensions Of Herpes Simplex Virus Type 1

Herpes simplex virus type 1 (HSV-1), the MacIntyre strain, was purchased from the American Type Culture Collection (ATCC) and propagated in Vero cells (ATCC) to a concentration of $10^6$–$10^7$ plaque forming units (PFU) per milliliter (ml). This solution was used as stock virus. A volume of 0.1–0.5 ml of stock virus was added to separate aliquots of modified Leibowitz medium ($L_{15}$ medium, Whittaker MA Bioproducts, and containing 2.5% or less of serum proteins) in order to give a PFU concentration between $10^5$ and $10^7$.

DiEd6Br in Cremophor EL (approximately 2.5 millimolar) was added to duplicate tubes of the virus-medium mixture. The concentrations of DiEd6Br employed were 0.0099, 0.0195, 0.039, 0.78, 0.156, 0.312, 0.625, 1.25, 2.5, 5.0 and 10.0 micromolar. Duplicate tubes representing each concentration of DiEd6Br in the medium-virus mixture were irradiated by light at a wave length of approximately 420 nm with a fluence of about 20 J/cm$^2$. Approximately 30–60 min elapsed between the addition of each concentration of DiEd6Br and exposure to light. During the holding period, the samples were maintained at 4° C. Except during the time of irradiation, all manipulations were carried out with minimal exposure to extraneous light. A sample of virus-medium mixture but not containing DiEd6Br was also irradiated under the same conditions. During the holding period and the period of irradiation, the duplicate samples of virus and medium containing different concentrations of DiEd6Br were held in the dark. In addition, samples of the three different samples containing different concentrations of DiEd6Br and a sample of the virus-medium mixture without DiEd6Br were also maintained in the dark.

Each sample including the stock virus were assayed on Vero cells for PFU/ml of HSV-1. The assay consisted of growing Vero cells in minimal essential medium with Hanks balanced salt solution supplemented with 10% fetal bovine serum, L-glutamine and antibiotics. Hepes buffer (2%) was added for growth in open plates (twelve well microplates from Co-star). Ten fold dilutions of each sample were prepared and 0.1 ml of the appropriate dilution for each individual sample was adsorbed at 37° C. for 1.5 hr. on a cell monolayer from which the growth medium had been removed. After the adsorption period, the cell monolayer was washed and an overlay consisting of equal volumes of 2X strength L-15 medium and 2% methylcellulose was added. Following an appropriate incubation time at 37° C. (about 4 days), the overlay medium was removed. Monolayers were fixed with methanol and stained with giemsa to elaborate the presence of plaques. The plaques were counted using a dissecting microscope at a magnification of 20X.

The results of the experiment can be observed in Table 15. It is clear that DiEd6Br in a concentration as low as 0.0195 mM, in combination with light at a wavelength of 420 #5 nm having an energy density of 20 J/cm$^2$, achieved a near total (larger than 99.99%) kill of HSV-1 in aqueous medium containing 2.5% or less of serum proteins. The use of larger amounts of DiEd6Br resulted in a similar reduction in viral infectivity. Vital-medium suspension samples containing the 8 different concentrations of DiEd6Br but which were not irradiated showed no evidence of cellular toxicity when assayed in the Vero cells as described above.

TABLE 15

Inactivation of HSV-1 with DiEd6BR (in Cremophor EL) and 20 J/cm2 of Light at 420 nm

| Sample | Irradiation | PFU/ml | Log$_{10}$ Reduction |
|---|---|---|---|
| HSV Control | No | $1.3 \times 10^6$ | |
| HSV + 10 µM DiEd6Br | No | $1.2 \times 10^6$ | 0.0348 |
| HSV + 2.5 µM DiEd6Br | No | $1.3 \times 10^6$ | 0.0 |
| HSV + .625 µM DiEd6Br | No | $1.0 \times 10^6$ | 0.1139 |
| HSV + .156 µM DiEd6Br | No | $1.1 \times 10^6$ | 0.0725 |
| Test #1 | | | |
| HSV Control | Yes | $9.9 \times 10^5$ | |
| HSV + 10 µM DiEd6Br | Yes | 0 | 5.9956 |
| HSV + 2.5 µM DiEd6Br | Yes | 0 | 5.9956 |
| HSV + .625 µM DiEd6Br | Yes | 0 | 5.9956 |
| HSV + .156 µM DiEd6Br | Yes | 0 | 5.9956 |
| Test #2 | | | |
| HSV Control | Yes | $7.4 \times 10^5$ | |
| HSV + .156 µM DiEd6Br | Yes | 0 | 5.8692 |
| HSV + .078 µM DiEd6Br | Yes | 0 | 5.8692 |
| HSV + .039 µM DiEd6Br | Yes | $9.9 \times 10^0$ | 4.8736 |
| HSV + .0195 µM DiEd6Br | Yes | $4.3 \times 10^1$ | 4.2358 |
| HSV + .0099 µM DiEd6Br | Yes | $4.0 \times 10^2$ | 3.2672 |

PFU: Plaque forming unit.
HSV-1: Diluted 1:10 in medium yielded $1.3 \times 10^5$ PFU/ml.
Virus diluted in blood and not irradiated yielded $1.0 \times 10^5$ PFU/ml.

(10) Effect Of DiEd6Br (Compound XLIV) And Light On Aqueous Suspensions Of Herpes Simplex Virus Type 1 Containing 15% Fetal Calf Serum Herpes simplex virus type 1 (HSV-1), the MacIntyre strain, was purchased from the American Type Culture Collection (ATCC) and propagated in Vero cells (ATCC) to a concentration of $10^6$–$10^7$ plaque forming units (PFU) per milliliter (ml). This solution was used as stock virus. A volume of 0.1–0.5 ml of stock virus was added to separate aliquots of modified Leibowitz medium ($L_{15}$ medium, Whittaker MA Bioproducts) containing approximately 15% fetal calf serum in order to give a PFU concentration between $10^5$ and $10^7$.

DiEd6Br in Cremaphor EL (Ethoxylated castor-bean oil, approximately 2.5 millimolar) was added to duplicate tubes of the virus-medium mixture. The concentrations of DiEd6Br employed were 0.078, 0.156, 0.312, 0.625, 1.25, 2.5, 5.0 and 7.5 micromolar. Duplicate tubes representing each concentration of DiEd6Br in the medium-virus mixture were irradiated by light at a wave length of approximately 420 nm with a fluence of about 20 J/cm$^2$. Approximately 30–60 minutes elapsed between the addition of each concentration of DiEd6Br and exposure to light. During the holding period, the samples were maintained at 4° C. Except during the time of irradiation, all manipulations were carried out with minimal exposure to extraneous light. A sample of virus-medium mixture but not containing DiEd6Br was also irradiated under the same conditions. During the holding period and the period of irradiation, the duplicate samples of virus and medium containing different concentrations of DiEd6Br were held in the dark. In addition, samples of the three different samples containing different concentrations of DiEd6Br and a sample of the virus-medium mixture without DiEd6Br were also maintained in the dark.

Each sample including the stock virus were assayed on Vero cells for PFU/ml of HSV-1. The assay consisted of growing Vero cells in minimal essential medium with Hanks balanced salt solution supplemented with 10% fetal bovine serum, L-glutamine and antibiotics. Hepes buffer (2%) was added for growth in open plates (twelve well microplates from CO-star). Ten fold dilutions of each sample were prepared and 0.1 ml of the appropriate dilution for each individual sample was adsorbed at 37° C. for 1.5 hr. on a cell monolayer from which the growth medium had been removed. After the adsorption period, the cell monolayer was washed and an overlay consisting of equal volumes of 2X strength L-15 medium and 2% methylcellulose was added. Following an appropriate incubation time at 37° C. (about 4 days), the overlay medium was removed. Monolayers were fixed with methanol and stained with giemsa to elaborate the presence of plaques. The plaques were counted using a dissecting microscope at a magnification of 20X.

The results of the experiment can be observed in Table 16. It is clear that DiEd6Br in a concentration as low as 0.156 mM, in combination with light at a wavelength of 420 #5 nm having an energy density of 20 J/cm$^2$, achieved a near total (larger than 99.99%) kill of HSV-1 in aqueous medium containing 2.5% or less of serum proteins. The use of larger amounts of DiEd6Br resulted in a similar reduction in viral infectivity. Vital-medium suspension samples containing the 8 different dye concentrations but which were not irradiated showed no evidence of cellular toxicity when assayed in the Vero cells as described above.

TABLE 16

Inactivation of HSV-1 in 15% Fetal Calf Serum with DiEd6Br (in Cremophor) and 20 J/cm2 of Light at 420 nm

| Sample | Irradiation | PFU/ml | Log$_{10}$ Reduction |
|---|---|---|---|
| HSV Control | Yes | $1.0 \times 10^5$ | |
| HSV + 10 μM DiEd6Br | Yes | 0 | ≧5 |
| HSV + 5 μM DiEd6Br | Yes | 0 | ≧5 |
| HSV + 2.5 μM DiEd6Br | Yes | 0 | ≧5 |
| HSV + 1.25 μM DiEd6Br | Yes | 0 | ≧5 |
| HSV + .625 μM DiEd6Br | Yes | $6.0 \times 10^1$ | 4.0 |
| HSV + .312 μM DiEd6Br | Yes | $8.5 \times 10^1$ | 3.1 |
| HSV + .156 μM DiEd6Br | Yes | $4.5 \times 10^3$ | 1.35 |
| HSV + .078 μM DiEd6Br | Yes | $4.2 \times 10^4$ | 0.38 |

PFU: Plaque forming unit.
HSV-1: Diluted 1:10 in medium yielded $1.0 \times 10^5$ PFU/ml.

(11) Effect Of Prior Activation Of Ed6Br (Compound VII) With 420 nm Light On Herpes Simplex Virus Type 1

Herpes simplex virus type 1 (HSV-1), the MacIntyre strain, was purchased from the American Type Culture Collection (ATCC) and propagated in Vero cells (ATCC) to a concentration of $2.7 \times 10^5$ plaque forming units (PFU) per milliliter (ml). This solution was used as stock virus.

Ed6Br in Cremophor EL was added to four separate aliquots of modified Liebowitz medium (L-15 medium, Whittaker MA Bioproducts) to give concentrations of 25 mM (2 aliquots) and 100 mM (2 aliquots), respectively, of the 1,8-naphthalimide. Two of the aliquots with 25 and 100 micromolar dye concentration, respectively, were irradiated with 420 #5 nm filtered radiation from a Xenon arc lamp at an irradiance of 20 mW/cm$^2$ for 166 minutes to give a total light fluence of 200 J/cm$^2$. The remaining two aliquots at 25 and 100 mM concentration were handled in duplicate fashion with aluminum foil wrapping but not illuminated. Immediately after illumination 100 microliter of stock HSV-1 suspension at $2.3 \times 10^5$ PFU/ml was added to each of the four samples containing the 1,8-naphthalimide compound. Each sample was held in the dark at 4° C. for 24 hr. prior to infectivity assay.

Each sample including the stock virus were assayed on Vero cells for PFU/ml of HSV-1. The assay consisted of growing Vero cells in minimal essential medium with Hanks balanced salt solution supplemented with 10% fetal bovine serum, L-glutamine and antibiotics. Hepes buffer (2%) was added for growth in open plates (twelve well microplates from CO-star). Ten fold dilutions of each sample were prepared and 0.1 ml of the appropriate dilution for each individual sample was adsorbed at 37° C. for 1.5 hr. on a cell monolayer from which the growth medium had been removed. After the adsorption period, the cell monolayer was washed and an overlay consisting of equal volumes of 2X strength L-15 medium and 2% methylcellulose was added. Following an appropriate incubation time at 37° C. (about 4 days), the overlay medium was removed. Monolayers were fixed with methanol and stained with giemsa to elaborate the presence of plaques. The plaques were counted using a dissecting microscope at a magnification of 20X.

The results of the experiment can be observed in Table 17. It is clear that Ed6Br in a concentration as low as 100 mM, with activation using light at a wavelength of 420 #5 nm having an energy density of 20 J/cm$^2$, prior to addition to the viral suspension, achieved a near total (larger than 99.99%) kill of HSV-1 in aqueous medium containing 2.5% or less of serum proteins. The viral-medium suspension samples containing the two different concentrations but which were not previously irradiated showed significantly less cellular toxicity than the irradiated samples when assayed in the Vero cells as described above.

TABLE 17

Inactivation of HSV-1 with Previously Activated Ed6Br

| Sample | Prior Activation | PFU/ml | Log$_{10}$ Reduction |
|---|---|---|---|
| HSV stock | — | $2.7 \times 10^5$ | — |
| HSV + 25 μM Ed6Br | + | $8.4 \times 10^3$ | 1.51 |
| HSV + 25 μM Ed6Br | — | $4.5 \times 10^4$ | 0.78 |
| HSV + 100 μM Ed6Br | + | $3.0 \times 10^1$ | 3.95 |
| HSV + 100 μM Ed6Br | — | $9.0 \times 10^3$ | 1.48 |

(12) Effect Of DiEd6Br (Compound XLIV) And Light On Aqueous Suspensions Of Herpes Simplex Virus Type 1 Containing 15% Fetal Calf Serum And Human Blood Platelets Herpes simplex virus type 1 (HSV-1), the MacIntyre strain, was purchased from the American Type Culture Collection (ATCC) and propagated in Vero cells (ATCC) to a concentration of $10^6$–$10^7$ plaque forming units (PFU) per milliliter (ml). This solution was used as stock virus. A volume of 0.1–0.5 ml of stock virus was added to separate aliquots of modified Leibowitz medium (L$_{15}$ medium, Whittaker MA Bioproducts) containing 15% added fetal calf serum proteins and human blood platelets at $2\times10^9$ per ml of viral suspension in order to give a PFU concentration between $10^5$ and $10^7$.

DiEd6Br in Cremaphor EL (approximately 2.5 millimolar) was added to duplicate tubes of the virus-medium mixture. The concentrations of DiEd6Br employed were 0.156 and 0.625 micromolar. Duplicate tubes representing each concentration of DiEd6Br in viral suspension were irradiated by light at a wave length of approximately 420 nm with fluence values of about 5, 10, 20, 40, and 60 J/cm². Approximately 30-60 min. elapsed between the addition of each concentration of DiEd6Br and exposure to light. During the holding period, the samples were maintained at 4° C. Except during the time of irradiation, all manipulations were carried out with minimal exposure to extraneous light. A sample of virus-medium mixture but not containing DiEd6Br was also irradiated under the same conditions. During the holding period and the period of irradiation, the duplicate samples of virus and medium containing different concentrations of DiEd6Br were held in the dark. In addition, samples of the three different samples containing different concentrations of DiEd6Br and a sample of the virus-medium mixture without DiEd6Br were also maintained in the dark.

Each sample including the stock virus were assayed on Vero cells for PFU/ml of HSV-1. The assay consisted of growing Vero cells in minimal essential medium with Hanks balanced salt solution supplemented with 10% fetal bovine serum, L-glutamine and antibiotics. Hepes buffer (2%) was added for growth in open plates (twelve well microplates from CO-star). Ten fold dilutions of each sample were prepared and 0.1 ml of the appropriate dilution for each individual sample was adsorbed at 37° C. for 1.5 hr. on a cell monolayer from which the growth medium had been removed. After the adsorption period, the cell monolayer was washed and an overlay consisting of equal volumes of 2X strength L-15 medium and 2% methylcellulose was added. Following an appropriate incubation time at 37° C. (about 4 days), the overlay medium was removed. Monolayers were fixed with methanol and stained with giemsa to elaborate the presence of plaques. The plaques were counted using a dissecting microscope at a magnification of 20X.

The results of the experiment can be observed in Table 18. It is clear that DiEd6Br in a concentration as low as 0.625 mM, in combination with light at a wavelength of 420 #5 nm having an energy density of 60 J/cm2, achieved a near total (larger than 99.86%) kill of HSV-1 in aqueous medium containing 15% of serum proteins and platelets at typical concentrations during blood bank storage. Vital suspension sample containing the 2 different concentrations and DiEd6Br but which were not irradiated showed no evidence of cellular toxicity when assayed in the Vero cells as described above.

TABLE 18

Inactivation of HSV-1 with DiEd6Br (in Cremophor EL) and 420 nm Light in 15% Fetal Calf Serum Containing Human Platelets

| Sample | Light Fluence (J/cm²) | PFU/ml | Log₁₀ Reduction |
|---|---|---|---|
| HSV Control | No | $7.6 \times 10^7$ | — |
| HSV + 625 μM DiEd6Br | 5 | $5.0 \times 10^5$ | 2.18 |
|  | 10 | $4.5 \times 10^5$ | 2.22 |
|  | 20 | $2.0 \times 10^4$ | 3.58 |
|  | 40 | $1.1 \times 10^3$ | 4.84 |
|  | 60 | None detected | 7 |

TABLE 18-continued

Inactivation of HSV-1 with DiEd6Br (in Cremophor EL) and 420 nm Light in 15% Fetal Calf Serum Containing Human Platelets

| Sample | Light Fluence (J/cm²) | PFU/ml | Log₁₀ Reduction |
|---|---|---|---|
| HSV + 0.156 μM DiEd6Br | 5 | $7.4 \times 10^7$ | 0.01 |
|  | 10 | $6.0 \times 10^7$ | 0.10 |
|  | 20 | $1.5 \times 10^7$ | 0.70 |
|  | 40 | $4.5 \times 10^6$ | 1.22 |
|  | 60 | $1.5 \times 10^6$ | 1.70 |

PFU: Plaque Forming Unit

(13) Effect Of DiEd6Br (Compound XLIV) And Light On Aqueous Suspensions Of Human Immunodeficiency Virus Human immunodeficiency virus (HIV) was propagated in the CEM T lymphoblastoid line A:301 as described previously by Chann et al (1986). Aliquots of cell-free HIV were prepared by centrifugation and resuspension in RPMI cell culture medium with a concentration of $1\times10^5$ IU (infectious units) per ml. Two aliquots having no DiE6Br but one being exposed to light served as E6Br free controls. DiE6Br was added to 6 additional aliquots of viral suspension to give concentrations of 1.25, 2.50, and 5.0 mM in each of a pair of samples, one member of each pair serving as the light free control. Following 30 min. delay, one sample at each of the listed DiE6Br concentrations was exposed at an irradiance of 20 mW/cm2 to give a light fluence of 20 J/cm² of 420 #5 nm radiation filtered from a xenon arc lamp, the other sample serving as dark control. After illumination 50 mL from each of the samples was transferred to individual wells of a 96-well flat bottomed plate in triplicate. To each sample well 50 mL of a suspension containing $5.0\times10^5$ MT-4 cells per ml are transferred and the culture plates incubated at 37.5° C. in a 50% $CO_2$ atmosphere. On the fourth day of incubation 100 mL of culture supernatant are removed and replaced with 100 mL of RPMI-1640 with 10% fetal calf serum.

Upon the seventh day of culture the infectivity of HIV is assayed using the MTT stain procedure which monitors the viability of the MT-4 cells. Viability of cell cultured with a treated viral sample is compared to that of an untreated control triplicate. Ten mL of the viability stain MTT [3-(4,5-dimethyl thiazole-2-yl) -2,5-diphenyltetrazolium bromide] at 5 mg/ml concentration in phosphate buffered saline (pH 7.3) is added directly to the MT-4 cells in culture. Cells are incubated for 4 hrs. after addition of the stain and 1.25 mL of 0.094 N HCl in nopropanol is added to develop the stain. The optical density of the layer of stained MT-4 cells lining the bottom of the sample well is read at 570 nm with a standard microplate reader (Coulter Company) and reading three empty wells as air blanks.

The results of the experiment can be viewed in Table 19. The essentially complete inactivation of HIV at DiEd6Br concentrations of 1.25 mM or greater is evident in the clearly approximate equality of the measured optical density read in virus free controls and the light treated samples containing DiEd6Br.

TABLE 19
Inactivation of Aqueous HIV Suspension with DiEd6Br and 420 nm Light

| Sample Number | DiEd6Br Concentration ($\mu M$) | Light Fluence ($J/cm^2$) | Optical Density* |
|---|---|---|---|
| 1 | 0 | 0 | 1.114 |
| 2 | 5 | 20 | 1.337 |
| 3 | 5 | 0 | 0.559 |
| 4 | 2.5 | 20 | 1.309 |
| 5 | 2.5 | 0 | 0.290 |
| 6 | 1.25 | 20 | 1.242 |
| 7 | 1.25 | 0 | 0.541 |

*Mean of O.D. values for triplicate sample wells
Reference:
Chanh T, Dreesman G, Kanda P, et al. Induction of anti-HIV neutralizing antibodies by synthetic peptides. EMBO J, 5:3065-71, 1986.

(14) Effect Of Ed6Br (Compound VII) And 420 nm Light On Aqueous Suspensions Of H9 Cells H9 cells (an immortal human T-cell lymphoma) were cultured in RPMI-1640 medium containing 10% additional fetal calf serum hold in air with a 5% $CO_2$ atmosphere at 37.5° C. to a cell density in the range of $10^5$-$10^7$ per ml. Cells were harvested by centrifugation and six 3-ml aliquots containing $1 \times 10^5$ H9 cells per ml suspended in 100% human were prepared. Ed6Br was added to four of the aliquots to give 5 and 25 mM concentrations, respectively, in each of two samples, and the samples allowed to set in the dark for 30 minutes. Single samples containing 0, 5, and 25 mM Ed6Br concentrations were irradiated with light of 420 #5 nm light filtered from a xenon arc lamp at 20 nW/$cm^2$ irradiance to give a light fluence of 10 J/$cm^2$. The remaining 3 samples wrapped in aluminum foil were handled identically but not irradiated. Immediately after irradiation, the cells in all samples were sedimented by centrifugation at $450 \times g$ for 10 minutes and the cell pellets individually resuspended to the original 3 ml volume of RPMI-1640 containing an additional 10% fetal calf serum plus Gentamycin antibiotic. The samples were incubated for 24 hr. under normal culture conditions cited above. Cell viability was assessed by Trypan Blue dye exclusion counts using a standard hemocytometer after 24 hr. incubation. The results of the experiment can be viewed in Table 20. Ed6Br concentrations of 5 mm or greater clearly inactivate or kill essentially 100% of H9 cells in suspension when activated by light but only approximately 10% or less of the cells were inactivated by Ed6Br at 25 mM concentration in the absence of light.

TABLE 20
Inactivation of H9 Cells (T-Cell Lymphoma) with Ed6Br and 420 nm Light

| Conditions | Live Cells | Dead Cells[a] | Cells/ml | % Viable |
|---|---|---|---|---|
| 0 $\mu M$ Ed6Br dark | 114 | 19 | $1.14 \times 10^6$ | 85.7 |
| 0 $\mu M$ Ed6Br irrad. | 82 | 11 | $8.20 \times 10^5$ | 88.2 |
| 5 $\mu M$ Ed6Br dark | 77 | 12 | $7.70 \times 10^5$ | 86.5 |
| 5 $\mu M$ Ed6Br irrad. | 0 | 47 | 0.0 | 0.0 |
| 25 $\mu M$ Ed6Br dark | 99 | 11 | $9.9 \times 10^5$ | 90.0 |
| 25 $\mu M$ Ed6Br irrad. | 0 | 41 | 0.0 | 0.0 |

[a]Identified by dark blue color due to Trypan Blue take-up.

(15) Tissue Bonding Experiments With DiEd6Br (Compound XLIV)

Bonding together of the overlapping surfaces of two strips of swine dura mater and of two thin slices of beef muscle with application of DiEd6Br in Cremophor EL as a carrier and irradiation with 420 #5 nm light filtered from a xenon arc lamp were studied.

Strips approximately $3 \times 0.5$ cm in dimension were cut from freshly harvested swine cranial dura mater, washed with 70% ethanol/water and blotted to dryness with standard chemical filter paper. External faces of each member of two pairs of strips were coated with a stock solution of Cremophor EL saturated at room temperature with DiEd6Br (approximately 2.5 millimolar), overlapped 1 cm with long axes parallel, and clamped between two Pyrex glass slides with edges of the slide-tissue-slide sandwich sealed with Parafilm. One sample was irradiated with 420 #5 nm light of 25 mW/$cm^2$ irradiance for 20 hrs. at room temperature to give a total light fluence of approximately 1800 J/$cm^2$. The companion sample was wrapped in aluminum foil for light shielding and placed alongside the irradiated sample for the duration of the experiment.

Following their respective irradiation or being held in the dark in similar temperature ambience, one end of a strip of each sample was clamped and from the other a Styrofoam container was hung by a clamp and fine suspension wires (weight of clamp plus container plus wires=33.3 gm). Weights (10 gm each) were added gently in a sequential fashion to give a total weight of 296.3 gm upon which the strip is separated at their interface within the overlapped region of the irradiated sample. Strips of the un-irradiated sample separated immediately at their interface under the 33.3 gm loading of the "weighing" container. This result indicates bonding of the two dura surfaces upon activation of DiEd6Br with light. Weight loading of the irradiated sample resulted in a uniform elongation and necking pattern of the overlapped region demonstrating uniform bonding of the overlapped surfaces. Elongation was approximately 50% at shearing of the interface. Upon separation, the strips rebounded to their nominal original shapes demonstrating no plastic deformation upon weight loading.

Computation of ultimate shear strength at failure (loading force at failure per overlap area) gave a value of 538 gm/$cm^2$ ($=1.5 \times 10^4$ Nt/$m^2$) which compares favorably with a value of 286 gm/$cm^2$ ($=0.8 \times 10^4$ Nt/$m^2$) obtained in thermally bonded human coronary artery immediately after treatment as described by Jenkins et al (1988).

Thin strips approximately 10 cm long, 1 cm wide, and 0.05–0.1 cm thick were sliced from beef steak obtained from a local meat market. Surfaces of the strips of two sample pairs were coated with a stock solution of DiEd6Br in Cremophor EL (0.1 millimolar concentration) and placed together to give approximately 2 cm overlap. One overlapping strip sample was irradiated for 24 hours with water-filtered (IR spectrum absorber) light from a 150 w xenon arc lamp. Beam diameter incident on the sample was approximately 3 cm. The other sample was wrapped in aluminum foil, placed alongside the irradiated sample, and served as dark control. Subsequent to irradiation, strips of the dark control separated under their own weight when hung vertically whereas discernable tactile finger pressure was felt when two hands were used to pull the irradiated strip apart, indicating bonding of the strip surface upon activation of DiEd6Br with light.

Both dura mater and the the sheaths of the muscle fibers comprising "steak" are connective tissues dominantly comprised of the protein collagen. The implications of these tissue bonding experiments is that use of the 1,8-naphthalimide dyes with activation serves to bond connective tissues (such as ligament, tendon, cornea of the eye, skin, arterial and venous walls, and duct walls such as of the vas deferens) together via protein crosslinking.

Reference:

R. D. Jenkins, I. N. Sinclair, R. Anand, A. G. Kalil, Jr., F. J. Schoen, and J. R. Spears. Laser Balloon Angioplasty: Effect of Tissue Temperature on Weld Strength of Human Postmortem Intima-Media Separations, *Lasers in Surg. and Med.* 3:30–39 (1988).

(16) Bleaching And Recovery Of The Fluorescence Of Ed6Br (Compound VII) And DiEd6Br (Compound XLIV)

Part I: Ed6Br Experiment:

A 14.9 millimolar stock solution of Ed6Br in Cremophor EL was used to make 3 ml of a micellar Cremophor suspension having a concentration averaged over the entire sample volume of 100 mM. A 100 mL aliquot was removed and diluted with 2.9 ml of distilled water for measurement of fluorescence using an SLM 500C spectrofluorometer (excitation, 420 nm, emission, 520 nm). The 3 ml sample was divided into two 1.5 ml aliquots placed in quartz crusetts. One sample was irradiated with stirring with 420 #5 nm filtered light from a xenon arc lamp with an irradiance of 20 mW/cm$^2$ and with the companion sample wrapped in aluminum foil (dark control) and maintained alongside of the irradiated sample. Aliquots of 100 mL volume were taken from each sample at times corresponding to illumination exposures of 10, 25, 50, 100, and 200 J/cm$^2$ (2 hr.47 min.) and their Ed6Br fluorescence determined immediately. After the entire light treatment, both the illuminated and dark control samples were divided into two equal aliquots and held pairwise (dark+previously illuminated) at 4° and 20° C. in the absence of light. Aliquots of 100 mL were taken from each sample after 18 and 43 hr. and their fluorescence emission values determined using the SLM 500C instrument immediately after sampling.

The effects of exposure to 420 nm light and subsequent holding of the un-irradiated and previously irradiated samples at 4° C. and 20° C. in the absence of light can be viewed in Table 21. The steady bleaching of the fluorescence emission intensity of Ed6Br during light exposure is evident, whereas the lack of change of the value of fluorescence emission intensity in the absence of light is also apparent. The ultimate recovery with time of the fluorescence intensity of Ed6Br while held at 22° C. and 4° C. are also evident with the rate of recovery increasing with temperature. These data indicate that an ultimate value of approximately 40% of the initial fluorescent intensity is regained after irradiation induced loss of about 80% of the fluorescent intensity during exposure to 200 J/cm$^2$.

Part II: DiEd6Br Experiment

In an experiment eventually following the protocol described immediately above in Part I (for Ed6Br), the light-induced bleaching of DiEd6Br with 200 J/cm$^2$ light exposure and recovery of its fluorescence upon standing in the dark at 22° C. were determined.

The fluorescence decreased to 32.2% of its initial (dark) value upon exposure to 200 J/cm$^2$ of 420 nm light and was found to have recovered to 62.7 and 64.0% of its initial value after being held for 70 and 166 hours at 22° C.

The light induced fluorescence bleaching arises from formation of the nonfluorescent activated g-halocrotonamide species of Ed6Br and DiEd6Br following illumination whereas the regained fluoresence arises from deactivation of the activated species not resulting from chemical reaction. Approximately 50% of the initially activated species recover in this fashion while the other 50% loose permanently their fluorescence upon entering into irreversible covalent reaction with a nucleophile, most probably the —OH group of the ricinoleate sidechains of Cremophor EL. The presence of the relatively long-lived chemically active g-halocrotonamide species, a highly efficient alkylating agent, in previously light activated Ed6Br- Cremophor and DiEd6Br-Cremophor mixtures suggests use of prior light activation of these 1,8-naphthalimide species to generate biologically active species for viral and cellular irradiation.

TABLE 21

Bleaching and Recovery of Ed6Br Fluorescence in Aqueous Suspension of Cremophor EL Part A: Fluorescence Bleaching in 420 ± 5 nm Light

| Light Fluence (J/Cm$^2$) | % Un-irradiated Fluorescence |
| --- | --- |
| 0 | 100 |
| 10 | 97.8 |
| 25 | 96.2 |
| 50 | 74.9 |
| 90 | 48.7 |
| 200 | 18.2 |

Part B: Fluorescence Recovery in Dark

| Recovery Time (Hour) | 4° C. Holding Temperature | 22° C. Holding Temperature |
| --- | --- | --- |
| 0 | 18.2 | 18.2 |
| 18 | 24.6 | 39.4 |
| 43 | 36.8 | 56.7 |

(17) Effects Of 420 nm Radiation On Liposomal-bound Gramacidin D And DiEd6Br (Compound XLIV)

Two milligram of the hydrophobic peptide Gramacidin D crystals and 8 milligrams of L-a-phosphatidyl choline dissolved in chloroform were mixed in a conical 50 ml glass centrifuge tube and evaporated to dryness under flowing nitrogen gas. Ten ml of phosphate buffered saline (pH=7.3) were added and mixed with a vortex mixer until no lipid layer remained on tube walls. The lipid suspension, having an average Gramacidin concentration of 111.1 mM, was then sonicated under nitrogen with cooling via immersion in ice water at a setting of 3 on a Heat Systems Sonicator with microtip. The resulting suspension of phosphatidyl choline liposomes (small unilaminar vesicles) containing Gramacidin D was divided into four 2 milliliter aliquots to which DiEd6Br (1 millimolar in Cremophor EL) was added to give average dye concentration of 0, 10, 20, and 50 mM concentration and maintained in the dark for 1 hr at 22° C. to allow partitioning of the dye into the liposomes. Each of the four 1 milliliter aliquots was divided into 0.5 milliliter aliquots, one for irradiation and one un-irradiated control. Irradiation was with 420#5 nm radiation at an irradiance of 30 mw/cm$^2$ to a fluence of 100 J/cm$^2$.

Following irradiation, both light-exposed and unexposed samples were diluted 1:20 in phosphate buffered saline (pH=7.3) for measurement of fluorescence emission intensity of both DiEd6Br and the tryptophan residues of Gramacidin D. Fluorescence was determined using an SLM 500C spectrofluorometer. For DiEd6Br excitation and emission wavelengths were 425 and 520 nm, respectively, and for the tryptophan residues of Gramacidin D, 290 and 340 nm, respectively.

The decrease in fluorescence emission intensity values of both the dye and tryptophan with light irradiation can be seen in Table 22. Loss of fluorescence intensity reflects the crosslinking to covalent bonding between the light activated form DiEd6Br and the nucleophilic tryptophan residues of Gramacidin D.

TABLE 22
Effects on DiEd6Br and Gramacidin D Fluorescences with 420 nm Light Irradiation

| Dye Conc. ($\mu$M) | DiEd6Br (ID/DD) %* | Tryptophan (IT/DT) %** |
|---|---|---|
| 0 $\mu$M DiEd6Br | 100 | 91.23 |
| 10 $\mu$M DiEd6Br | 5.03 | 10.57 |
| 20 $\mu$M DiEd6Br | 9.24 | 10.77 |
| 50 $\mu$M DiEd6Br | 20.26 | 14.40 |

*, **Ratios of irradiated and un-irradiated fluorescent omission intensities of dye (D) and tryptophan (T)

(18) Take-Up Of Ed6Br (Compound VII) And DiEd6Br (Compound XLIV) By H9 Cells (T-Cell Lymphoma)

H9 cells (an immortal human T-cell lymphoma) were cultured in RPMI-1640 medium containing 10% additional fetal calf serum held in air with a 5% $CO_2$ atmosphere at 37.5° C. to a cell density in the range of $10^5$–$10^7$ per ml. Cells were harvested by centrifugation and four 3-milliliter aliquots containing $5 \times 10^5$ H9 cells per ml suspended in RPM 1-1640 medium with 10% additional fetal calf serum were prepared. Ed6Br was added to three aliquots to give 5, and 25 mM concentrations, respectively. The fourth aliquot served as a dye-free control. Immediately after addition of the dyes, 1 ml samples were harvested from each aliquot and the cells washed by dilution into 3 ml phosphate buffered saline (pH 7.3), followed by two repetitions of centrifugation, decantation of the supernatant, and resuspension of the cell pellet in the buffered saline solution, and a final centrifugation, decantation, and retention of the cell pellet at 4° C. for subsequent analysis. At the subsequent elapsed incubation times at 1, 2, 3, and 4 hrs., one milliliter samples were harvested and treated in an identical fashion. After treatment of the 4-hr. sample, the cells of each sample were lysed in 3 ml of an 0.1% solution of ctyltetraammonium bromide detergent in phosphate buffered saline (pH=7.3). The fluorescence emission at 520 nm (420 nm excitation) of each sample was determined with a SLM SPT 500C spectrofluorometer. Additionally, the emission intensity of samples of these detergent solutions having, respectively, dye concentrations. of 0, 0.1, 0.2, 0.5, 0.8, 1.0, 1.2, 1.5, 2, 3, 4, and 5 mM were prepared as standards for calibrating the concentration dependence of the fluorescence emission. These data were used with the fluorescence emission intensity values obtained from the cell samples to determine the total concentration of dye taken up by the $5 \times 10^5$ ml H9 cells in each cell aliquot, and then the average quantity of dye sequestered per cell at the various exposure times and external dye concentrations was computed.

The results can be viewed in Table 23. The increase and saturation in amount of Ed6Br taken-up with increasing exposure time and the increase with external dye concentration are readily discerned. Using an average diameter of 12 micron for the H9 cell determined in our laboratory using light microscopy, the average dye concentration in the H9 cell can be estimated from the total number of moles taken-up per cell. For example, a 4 hr. exposure to an external Ed6Br concentration of 25 mM resulted in take-up of Ed6Br by the average H9 cell to result a concentration of about 1.92 millimolar, approximately 77 times greater than the external concentration. Similar calculation of average cellular concentration after four hr exposure for exposure to 1 and 5 mm external concentration of Ed6Br resulted also in approximately a 70-fold increased concentration of the dye by the cell.

TABLE 23
Time Dependent Up-take of Ed6Br by H9 Cells (T-Cell Lymphoma at 22° C.)

| Exposure Time (hr.) | External Ed6BR Concentration ($\mu$M) | Cellular Ed6Br ($a^\circ$mol/cell)$^{(a)}$ |
|---|---|---|
| 0 | 1 | 91.2 |
| 1 | | 130.2 |
| 2 | | 189.8 |
| 3 | | 186.0 |
| 4 | | 208.3 |
| 0 | 5 | 165.6 |
| 1 | | 385.1 |
| 2 | | 437.2 |
| 3 | | 468.8 |
| 4 | | 548.9 |
| 0 | 25 | 316.2 |
| 1 | | 716.3 |
| 2 | | 1073.4 |
| 3 | | 1689.3 |
| 4 | | 1748.8 |

$^{(a)}$1 $a^\circ$mol = $1 \times 10^{-18}$ mol

(19) Effects On H9 Cells (T-cell Lymphoma) Of Ed6Br (Compound VII) in Cremophor EL With Prior Activation BF 420±5 nm Light H9 cells were cultivated in RPMI-1640 medium containing an additional 10% fetal calf serum at 37.5° C. in air having added 5% $CO_2$. A 5.46 ml aliquot of cell suspension containing $9.16 \times 10^5$ H9 cells per ml was harvested, the cells sedimented at $450 \times g$ for 10 minutes and resuspended in fresh growth medium. Two hundred microliter aliquots of the suspension were centrifuged as above and the resulting cell pellet served for resuspension in dye plus medium suspension for this study.

Six milliliters of suspension of Cremophor EL micelles containing Ed6Br in RPMI-1640 containing 10% additional fetal calf serum was made by diluting a 2.5 millimeter solution of the dye in Cremophor EL to give an average Ed6Br concentration of 100 mM, and the resulting suspension divided into 2 three milliliter aliquots. One aliquot was irradiated with 420±5 nm light filtered from a xenon arc lamp at an irradiance of 20 mW/cm$^2$ to a total fluence of 200 J/cm$^2$. The companion aliquot was wrapped in aluminum foil and handled in identical fashion to the irradiated sample. These two aliquots served as stocks for deforming effects of both previously irradiated and un-irradiated Ed6Br at different concentrations from 0 up to 100 mM on H9 cells kept in the dark. Dilutions of the stock dye suspension into additional fresh growth medium were made within 1 hour of light irradiation to give dye-medium suspensions with average Ed6Br concentrations of 0, 1, 10, 25, 50, 75, and 200 mM for both previously irradiated and dark dye samples. The H9 cell pellets were resuspended in these dye-Cremophor EL suspensions and held at 37.5° C. in an air atmosphere containing an additional 5% $CO_2$. After 24 hrs culture of the number of total and viable H0 cells was determined by Trypan Blue exclusion using a hemocytometer and microscope for cell counting, The number of killed cells was determined as those exhibiting the blue dye color, See Table 24.

TABLE 24

Inactivation of H9 Cells (T-Cell Lymphoma) with Ed6BR Previously Activated with 420 nm Light

| Ed6BR Concentration (uM) | Previous Light Activation | % Viable Cells |
|---|---|---|
| 0 | No | 72.6 |
| 1 | No | 72.7 |
| 1 | Yes | 68.4 |
| 10 | No | 77.2 |
| 10 | Yes | 31.8 |
| 25 | No | 57.9 |
| 25 | Yes | 4.9 |
| 50 | No | 27.4 |
| 50 | Yes | 0.0 |
| 75 | No | 33.9 |
| 75 | Yes | 0.0 |
| 100 | No | 28.0 |
| 100 | Yes | 0.0 |

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hererto.

What is claimed is:

1. A method for eradicating a pathogenic biological contaminant from a target body tissue, said method comprising:
   admixing said target body tissue with an effective amount of:
   a non-azo N-substituted-1,8-naphthalimide compound substituted by, at a 3-position, a nucleofuge and, at a 4-position, a heteroatomic electron-releasing group, said heteroatomic electron-releasing group being characterized as having a heteroatom directly linked to said 4-position and having at least one hydrogen directly attached to said heteroatom, said non-azo N-substituted-1,8-naphthalimide compound being characterized as predominantly hydrophobic and, after being activated by a sufficient amount of activating agent gives an activated derivative,
   or a pharmaceutically acceptable salt thereof, to give a resultant body tissue;
   activating said resultant body tissue with a sufficient amount of an activating agent so as to eradicate said pathogenic biological contaminant.

2. The method of claim 1 wherein said body tissue is body fluid, packed red blood cell, packed white blood cell, cryo precipitate from blood plasma, plasma protein, skin or cornea.

3. The method of claim 2 wherein said body fluid is whole blood, blood plasma, serum, fluid from plasmapheresis, bone marrow or plasma fibrinogen.

4. The method of claim 2 wherein said body fluid is albumin, gamma globulin or semen.

5. The method of claim 1 wherein said body tissue is platelet.

6. The method of claim 1 wherein said pathogenic biological contaminant is virus, tumor cell, bacterium or parasite.

7. A method for eradicating a pathogenic biological contaminant from a target body tissue, said method comprising:
   admixing said target body tissue with an effective amount of:
   a non-azo N-substituted-1,8-naphthalimide compound having at least two 1,8-naphthalimide moieties each substituted by, at a 3-position, a nucleofuge and, at a 4-position, a heteroatomic electron-releasing group, said heteroatomic electron-releasing group being characterized as having a heteroatom directly linked to said 4-position and having at least one hydrogen directly attached to said heteroatom, said non-azo N-substituted-1,8-naphthalimide compound being characterized as predominantly hydrophobic and, after being activated by a sufficient amount of activating agent, gives an activated derivative,
   or a pharmaceutically acceptable salt thereof, to give a resultant body tissue;
   activating said resultant body tissue with a sufficient amount of an activating agent so as to eradicate said pathogenic biological contaminant.

8. The method of claim 7 wherein said body tissue is body fluid, packed red blood cell, packed white blood cell, cryo precipitate from blood plasma, plasma protein, skin or cornea.

9. The method of claim 8 wherein said body fluid is whole blood, blood plasma, serum, fluid from plasmapheresis, bone marrow or plasma fibrinogen.

10. The method of claim 8 wherein said body fluid is albumin, gamma globulin or semen.

11. The method of claim 7 wherein said body tissue is platelet.

12. The method of claim 7 wherein said pathogenic biological contaminant is virus, tumor cell, bacterium or parasite.

13. A method for eradicating a pathogenic biological contaminant from a target body tissue, said method comprising:
   activating, with a sufficient amount of an activating agent,
   a non-azo N-substituted-1,8-naphthalimide compound substituted by, at a 3-position, a nucleofuge and, at a 4-position, a heteroatomic electron-releasing group, said heteroatomic electron-releasing group being characterized as having a heteroatom directly linked to said 4-position and having at least one hydrogen directly attached to said heteroatom, said non-azo N-substituted-1,8-naphthalimide compound being characterized as predominantly hydrophobic and, after being activated by a sufficient amount of activating agent gives an activated derivative,
   or a pharmaceutically acceptable salt thereof, to give a resultant activated compound; and
   admixing a sufficient amount of said resultant activated compound with said target body tissue to eradicate said pathogenic biological contaminant in said target body tissue.

14. The method of claim 13 wherein said body tissue is body fluid, packed red blood cell, packed white blood cell, cryo precipitate from blood plasma, plasma protein, skin or cornea.

15. The method of claim 14 wherein said body fluid is whole blood, blood plasma, serum, fluid from plasmapheresis, bone marrow or plasma fibrinogen.

16. The method of claim 14 wherein said body fluid is albumin, gamma globulin or semen.

17. The method of claim 13 wherein said body tissue is platelet.

18. The method of claim 13 wherein said pathogenic biological contaminant is virus, tumor cell, bacterium or parasite.

19. A method for eradicating a pathogenic biological contaminant from a target body tissue, said method comprising:

activating, with a sufficient amount of an activating agent, a non-azo N-substituted-1,8-naphthalimide compound having at least two 1,8-naphthalimide moieties each substituted by, at a 3-position, a nucleofuge and, at a 4-position, a heteroatomic electron-releasing group, said heteroatomic electron-releasing group being characterized as having a heteroatom directly linked to said 4-position and having at least one hydrogen directly attached to said heteroatom, said non-azo N-substituted-1,8-naphthalimide compound being characterized as predominantly hydrophobic and, after being activated by a sufficient amount of activating agent, gives an activated derivative, or a pharmaceutically acceptable salt thereof, to give a resultant activated compound; and admixing a sufficient amount of said resultant activated compound with said target body tissue to eradicate said pathogenic biological contaminant in said target body tissue.

20. The method of claim 19 wherein said body tissue is body fluid, packed red blood cell, packed white blood cell, cryo precipitate from blood plasma, plasma protein, skin or cornea.

21. The method of claim 20 wherein said body fluid is whole blood, blood plasma, serum, fluid from plasmapheresis, bone marrow, or plasma fibrinogen.

22. The method of claim 20 wherein said body fluid is albumin, gamma globulin or semen.

23. The method of claim 19 wherein said body tissue is platelet.

24. The method of claim 19 wherein said pathogenic biological contaminant is virus, tumor cell, bacterium or parasite.

* * * * *

UNITED STATES PATENT AND TRADEMARK OFFICE
CERTIFICATE OF CORRECTION

PATENT NO. : 5,420,136
DATED : May 30, 1995
INVENTOR(S) : Lewis et al.

It is certified that error appears in the above-indentified patent and that said Letters Patent is hereby corrected as shown below:

Col. 3, line 20, following "1 aa to", insert "1".

Col. 3, line 23, delete "to" and insert therefore -- and --.

Col. 4, line 18, delete "(n-1" and insert therefore -- (n=1 --.

Col. 4, line 53, between "$1 \leq p \leq 10$" and "$0 \leq q \leq 2m$" insert therefore -- , --.

Col. 5, line 16, delete "ArCH" and insert therefore -- $ArC_nH$ --.

Col. 5, line 62, delete "$C_nH_2m+1$" and insert therefore -- $C_nH_{2m+1}$, --.

Col. 5, line 64, following "$0 \leq q \leq 2m$", insert -- ) --.

Col. 8, line 21, delete "ArCH" and insert therefore -- $ArC_nH$ --.

Col. 9, line 1, following "$0 \leq q \leq 2m$", insert -- ) --.

Col. 9, line 30, delete "(n-1" and insert therefore -- (n=1 --.

UNITED STATES PATENT AND TRADEMARK OFFICE
CERTIFICATE OF CORRECTION

PATENT NO. : 5,420,136
DATED : May 30, 1995
INVENTOR(S) : Lewis et al.

It is certified that error appears in the above-indentified patent and that said Letters Patent is hereby corrected as shown below:

Col. 9, line 35, delete "$C_{nH2m}$" and insert therefore -- $C_nH_{2m}$ --.

Col. 9, line 37, delete "$C_nH_{qF2m-q}$" and insert therefore -- $C_nH_qF_{2m-q}$ --.

Col. 12, line 28, following "equivalent", delete -- . --.

Col. 13, in the second table, under the heading "R and R'", delete "$n-C_9H_{18}$" and insert therefore -- $n-C_9H_{19}$ --.

Col. 15, line 26, delete "crosslinking" and insert therefore -- cross-linking --.

Col. 18, in Table 2, in the second line of the heading, delete "31".

Col. 18, line 61, delete "0°" and insert therefore -- 20° --.

Col. 21, line 2, following "medium", delete ",".

Col. 22, following Table 10, insert --The results tabulated in Tables 8, 9 and 10 show that Compound VII is a potent mediator of photochemical toxicity, and a highly efficient photochemical cell --

UNITED STATES PATENT AND TRADEMARK OFFICE
CERTIFICATE OF CORRECTION

PATENT NO. : 5,420,136
DATED : May 30, 1995
INVENTOR(S) : Lewis et al.

It is certified that error appears in the above-indentified patent and that said Letters Patent is hereby corrected as shown below:

Col. 22, line 38, delete "32 mm" and insert therefore -- 32 mM --.

Col. 23, line 15, delete "sere-free" and insert therefore -- serum-free --.

Col. 24, line 46, following "concentration", delete -- , --.

Col. 25, line 19, delete "Vital-" and insert therefore -- Viral-. --.

Col. 26, line 13, delete "(HI)L)" and insert therefore -- (HDL) --.

Col. 26, in Table 14, under 1(b), in the 5th line of the 4th column, delete "1 M-protein" and insert therefore --2 M-protein--.
-- 2M-protein --.

Col. 28, line 8, delete "Vital-" and insert therefore -- Viral- --.

Col. 29, line 33, delete "Vital-" and insert therefore -- Viral- --.

Col. 30, following "illuminated." insert a paragraph break.

UNITED STATES PATENT AND TRADEMARK OFFICE
CERTIFICATE OF CORRECTION

PATENT NO. : 5,420,136
DATED : May 30, 1995
INVENTOR(S) : Lewis et al.

It is certified that error appears in the above-indentified patent and that said Letters Patent is hereby corrected as shown below:

Col. 31, line 52, delete "Vital" and insert therefore -- Viral --.

Col. 32, line 21, delete "Chann" and insert therefore -- Chanh --.

Col. 33, line 25, delete "3-ml" and insert therefore -- 3ml --.

Col. 33, line 26, following "100% human", insert -- serum --.

Col. 33, line 46, delete "5 mm" and insert therefore -- 5 mM --.

Col. 35, line 38, following "4°", insert -- C. --.

Col. 36, line 16, delete "Ed6Br- Cremophor" and insert therefore -- Ed6Br-Cremophor --.

Col. 37, line 33, delete "5x105" and insert therefore -- $5 \times 10^5$ --.

Col. 37, line 34, delete "1-1640" and insert therefore -- I-1640 --.

UNITED STATES PATENT AND TRADEMARK OFFICE
CERTIFICATE OF CORRECTION

PATENT NO. : 5,420,136
DATED : May 30, 1995
INVENTOR(S) : Lewis et al.

It is certified that error appears in the above-indentified patent and that said Letters Patent is hereby corrected as shown below:

Col. 37, line 56, following "centrations", delete -- . --.

Col. 38, line 38, delete "BF" and insert therefore -- By --.

Col. 39, line 7, delete "counting," and insert therefore -- counting. --.

Col. 39, in Table 24, delete "(uM)" and insert therefore -- ($\mu$M) --.

Signed and Sealed this

Eleventh Day of June, 1996

Attest:

BRUCE LEHMAN

Attesting Officer

Commissioner of Patents and Trademarks